United States Patent
Kasa et al.

(10) Patent No.: US 9,941,177 B2
(45) Date of Patent: Apr. 10, 2018

(54) PATTERN ACCURACY DETECTING APPARATUS AND PROCESSING SYSTEM

(71) Applicant: TOSHIBA MEMORY CORPORATION, Tokyo (JP)

(72) Inventors: Kentaro Kasa, Yokkaichi Mie (JP); Kazuya Fukuhara, Suginami Tokyo (JP); Kazutaka Ishigo, Yokkaichi Mie (JP); Manabu Takakuwa, Tsu Mie (JP); Yoshinori Hagio, Kuwana Mie (JP); Kazuhiro Segawa, Kuwana Mie (JP); Yuki Murasaka, Yokkaichi Mie (JP); Tetsuya Kugimiya, Kawasaki Kanagawa (JP); Yuu Yamayose, Shinjuku Tokyo (JP); Yosuke Okamoto, Sagamihara Kanagawa (JP)

(73) Assignee: Toshiba Memory Corporation, Tokyo (JP)

( * ) Notice: Subject to any disclaimer, the term of this patent is extended or adjusted under 35 U.S.C. 154(b) by 0 days.

(21) Appl. No.: 15/253,476

(22) Filed: Aug. 31, 2016

(65) Prior Publication Data

US 2017/0271214 A1    Sep. 21, 2017

(30) Foreign Application Priority Data

Mar. 16, 2016   (JP) .................................. 2016-052906

(51) Int. Cl.
  *H01L 21/00*   (2006.01)
  *H01L 21/66*   (2006.01)
  (Continued)

(52) U.S. Cl.
  CPC .............. *H01L 22/20* (2013.01); *G01B 11/27* (2013.01); *G01B 11/306* (2013.01); *G01N 25/72* (2013.01);
  (Continued)

(58) Field of Classification Search
  CPC .............. H01L 22/20; H01L 21/67248; H01L 21/67288; H01L 21/0274; G01B 11/306;
  (Continued)

(56) References Cited

U.S. PATENT DOCUMENTS 5,539,521 A * 7/1996 Otokake ............. G03F 7/70691
                                                250/559.29
5,872,694 A * 2/1999 Hoinkis ................. H02N 13/00
                                                361/234

(Continued)

FOREIGN PATENT DOCUMENTS

| JP | H04-181945 | 6/1992 |
|----|------------|--------|
| JP | 2006-024681 | 1/2006 |
| JP | 2011-040547 | 2/2011 |

OTHER PUBLICATIONS

"Tencor® FLX-2320 Thin Film Stress Measurement User Manual"; Software Version 4.2, Rev. B, Sep. 1995.*

*Primary Examiner* — Vu A Vu

(74) *Attorney, Agent, or Firm* — Patterson & Sheridan, LLP

(57) ABSTRACT

A pattern accuracy detecting apparatus includes a stage for supporting a substrate, an optical warpage detecting unit that measures a shape of a substrate disposed on the stage, an optical pattern detection unit that detects a position of a pattern on the substrate, and a processing unit that corrects the detected pattern position based on the measured shape of the substrate.

13 Claims, 16 Drawing Sheets

(51) Int. Cl.
*G01B 11/27* (2006.01)
*G01B 11/30* (2006.01)
*G01N 25/72* (2006.01)
*H01L 21/67* (2006.01)
*H01L 21/027* (2006.01)
*G03F 7/20* (2006.01)
*G03F 7/039* (2006.01)
*G03F 7/26* (2006.01)

(52) U.S. Cl.
CPC ............... *G03F 7/039* (2013.01); *G03F 7/20* (2013.01); *G03F 7/26* (2013.01); *H01L 21/0274* (2013.01); *H01L 21/67248* (2013.01); *H01L 21/67288* (2013.01); *G01B 2210/56* (2013.01)

(58) Field of Classification Search
CPC .... G01B 11/27; G01B 2210/56; G01N 25/72; G03F 7/20; G03F 7/039; G03F 7/26

USPC .............................................................. 438/5
See application file for complete search history.

(56) References Cited

U.S. PATENT DOCUMENTS

| | | | |
|---|---|---|---|
| 6,713,824 B1* | 3/2004 | Mikata | ................... C23C 16/24 257/407 |
| 7,955,074 B2* | 6/2011 | Jin | ................... H01L 21/67109 432/247 |
| 7,957,827 B2* | 6/2011 | Shih | ........................ H01L 22/12 438/5 |
| 8,482,719 B2 | 7/2013 | Van Eijk et al. | |
| 8,917,489 B2* | 12/2014 | Shu | ................... H01L 21/67288 361/234 |
| 8,952,297 B2* | 2/2015 | He | ................... H01L 21/67115 118/728 |
| 9,164,405 B2 | 10/2015 | Sasaki | |
| 2014/0107998 A1 | 4/2014 | Vukkadala et al. | |

\* cited by examiner

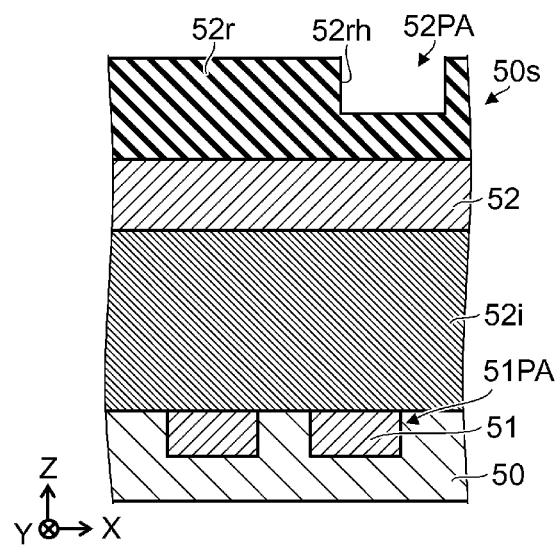
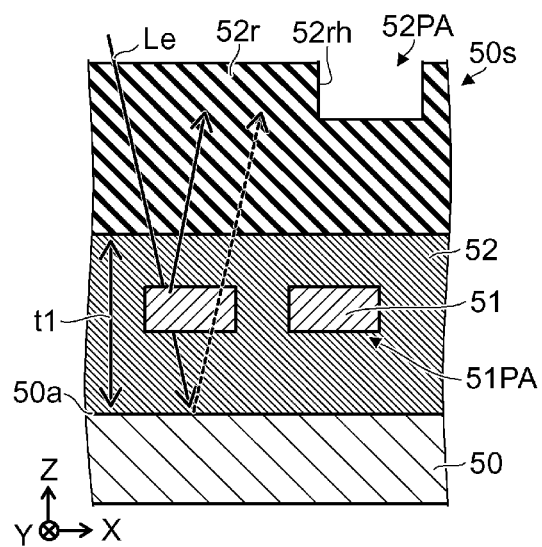

PATTERN ACCURACY DETECTING APPARATUS AND PROCESSING SYSTEM

CROSS-REFERENCE TO RELATED APPLICATION

This application is based upon and claims the benefit of priority from Japanese Patent Application No. 2016-052906; filed Mar. 16, 2016, the entire contents of which are incorporated herein by reference.

FIELD

Embodiments described herein relate generally to a pattern accuracy detecting apparatus and a processing system.

BACKGROUND

A plurality of layers are stacked in a semiconductor device. It is required to detect an alignment error of patterns between the plurality of layers with high accuracy.

DESCRIPTION OF THE DRAWINGS

FIG. 4A to FIG. 4D are schematic views exemplifying detection of accuracy of a substrate pattern.

DETAILED DESCRIPTION

Figure 1:
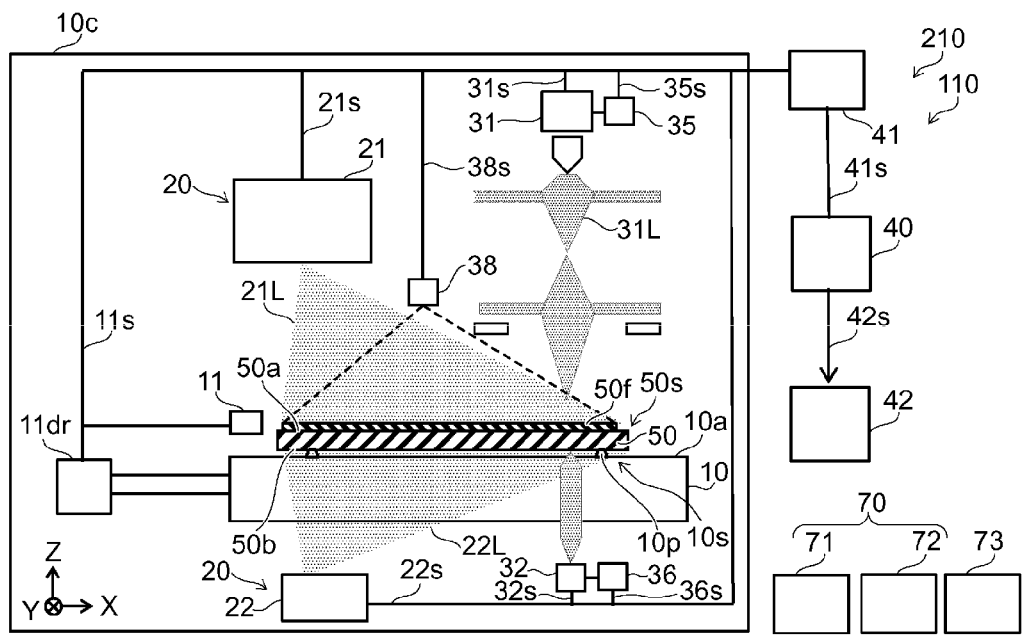
FIG. 1 is a schematic view exemplifying a pattern accuracy detecting apparatus according to a first embodiment.

An embodiment provides a pattern accuracy detecting apparatus which is capable of detecting alignment error with high accuracy, and a processing system.

A pattern accuracy detecting apparatus according to one embodiment includes a stage for supporting a substrate, an optical warpage detecting unit that measures a shape of a substrate disposed on the stage, an optical pattern detection unit that detects a position of a pattern on the substrate, and a processing unit that corrects the detected pattern position based on the measured shape of the substrate.

A pattern accuracy detecting apparatus according to another embodiment includes a warpage detecting unit and a processing unit. The warpage detecting unit detects first warpage in a first state of a substrate and second warpage in a second state of the substrate. A first film including a first pattern is disposed on a first surface of the substrate in the first state. A second film including a second pattern is disposed on the first surface in the second state. The processing unit derives a value in accordance with a difference between a position inside the first surface of the first pattern and a position inside the first surface of the second pattern in the second state, based on first information relating to the first warpage, second information relating to the second warpage, third information relating to the position inside the first surface of the first pattern in a third state of warpage different from the first warpage in which the first film is disposed on the first surface, and fourth information relating to the position inside the first surface of the second pattern in a fourth state of warpage different from the second warpage in which the second film is disposed on the first surface.

Hereinafter, each exemplary embodiment will be described with reference to drawings.

The drawings are schematic, exemplary, or conceptual, and dimensions, thicknesses, widths, and ratios thereof may vary in different embodiments.

In the specification and each drawing, the same reference numeral is used to identify the same element in all the drawings, and detailed description will be appropriately omitted where redundant.

First Embodiment

FIG. 1 is a schematic view exemplifying a pattern accuracy detecting apparatus according to a first embodiment.

The pattern accuracy detecting apparatus 110 according to the embodiment includes a warpage detecting unit 20, and a processing unit 40. The processing unit 40 includes, for example, a computer.

The apparatus 110 has a chamber 10c, which can be internally pumped down to sub-atmospheric pressure. The warpage detecting unit 20 is disposed inside of the chamber 10c. In this example, the processing unit 40 is disposed outside the chamber 10c.

A stage 10 is disposed inside the chamber 10c. A wafer 50s is disposed on an upper surface 10a of the stage 10. At least a part of the upper surface 10a of the stage 10 is, for example, flat.

In the embodiment, let a vertical direction with respect to the upper surface 10a of the stage 10 be a Z axis direction. Let a horizontal direction with respect to the Z axis direction be an X axis direction. Let a horizontal direction perpendicular to the Z axis direction and the X axis direction be a Y axis direction. The X, Y, and Z axes define a coordinate system of the pattern accuracy detecting apparatus 110 irrespective of directional terms such as "vertical" and "horizontal."

For example, a pin 10p is included in the stage 10. The pin 10p can be movable along the Z axis direction, which may be vertical. Three or more pins 10p may be included. When the pin 10p is located at the upper surface 10a, the three pins 10p support the wafer 50s. Each pin 10p is an example of a supporting unit 10s. In general, the wafer 50s is supported by one or more supporting units 10s. As described later, other mechanisms may be used as the supporting unit 10s.

When the pin 10p is located at the upper surface 10a, and the wafer 50s is supported by the pin 10p, stress is not applied substantially to the wafer 50s. If the wafer 50s is warped, the wafer 50s is in a non-flat state in accordance with the warpage because no force is applied to the wafer 50s to make it adhere to the flat upper surface 10a.

Meanwhile, when the pin 10p is not on the upper surface 10a, the wafer 50s may be removably adhered to the stage 10, for example, by electrostatic force. Even when the wafer 50s is warped, the wafer 50s may assume the shape of the upper surface 10a of the stage 10 due to the adhesive force. For example, the wafer 50s becomes substantially parallel to the upper surface 10a when adhered to the upper surface 10a by electrostatic force.

The wafer 50s includes a substrate 50. The substrate 50 is, for example, a semiconductor substrate (for example, silicon substrate). The substrate 50 includes a first surface 50a and a second surface 50b. The second surface 50b is a surface opposite to the first surface 50a. For example, the first surface 50a is an upper surface, and the second surface 50b is a lower surface (rear surface). Various films 50f are disposed on the first surface 50a.

For example, the warpage detecting unit 20 includes at least one of a first surface shape measuring unit 21 and a second surface shape measuring unit 22. The first surface shape measuring unit 21 emits, for example, light 21L to the first surface 50a of the substrate 50. Any warpage of the substrate 50 affects the light 21L reflected from first surface 50a, so the reflected light is modulated. Warpage of the substrate 50 can be detected by detecting the modulated light 21L. The second surface shape measuring unit 22 emits, for example, light 22L to the second surface 50b of the substrate 50. Warpage of the substrate 50 likewise affects the light 22L reflected from the second surface 50b, so the reflected light is modulated. Warpage of the substrate 50 can also be detected by detecting the modulated light 22L. When the second surface shape measuring unit 22 is used, the light 22L may be transmitted through the stage 10. Thus, each of the first surface shape measuring unit 21 and the second surface shape measuring unit 22 is an optical reflection unit, and the warpage detection unit, which is a substrate shape detection unit, is an optical reflection unit.

In the embodiment, warpage (surface shape) of the first surface 50a may be detected, warpage (surface shape) of the second surface 50b may be detected, or warpage of both the warpage of the first surface 50a and the warpage of the second surface 50b may be detected and an average of these detected values may be used.

In this example, a stage moving unit 11dr, a stage position detecting unit 11, and a first pattern detecting unit 31 are disposed inside the chamber 10c.

A position of the stage 10 is changed by the stage moving unit 11dr. The position of the stage 10 includes a position inside an X-Y plane. The position of the stage may further include a position along the Z axis direction. The stage position detecting unit 11 detects the position of the stage 10.

As described later, various patterns are formed in or on the film 50f. The first pattern detecting unit 31 detects a position of a pattern disposed in or on the film 50f. The first pattern detecting unit 31 includes, for example, an imaging element, which detects the pattern disposed on the substrate 50 (film 50f). For example, a position of the stage 10 is fixed by the stage moving unit 11dr, enabling the first pattern detecting unit 31 to detect the pattern of the wafer 50s disposed on the stage 10. Detection of the pattern includes detection of an X-Y position of the pattern, for example, an X axis coordinate and a Y axis coordinate of the pattern.

In this example, information relating to warpage detected by the warpage detecting unit 20, information relating to the position of the stage 10 detected by the stage position detecting unit 11, and information relating to the position of the pattern detected by the first pattern detecting unit 31 are supplied to a first database 41. The information (data) supplied to the first database is supplied to the processing unit 40. In the processing unit 40, for example, information relating to an alignment error of various films 50f is processed, and resulting data is stored in a second database 42.

In the embodiment, the warpage detecting unit 20 is capable of detecting the warpage of the substrate 50 (wafer 50s) multiple times. For example, the warpage detecting unit 20 can detect a first warpage of the substrate 50 in a first state and a second warpage of the substrate 50 in a second state. In the first state, a first film (a part of the film 50f) which includes a first pattern is disposed on the first surface 50a of the substrate 50. In the second state, a second film (another part of film 50f) which includes a second pattern is disposed on the first surface 50a. First information relating to the first warpage and second information relating to the second warpage are obtained by the warpage detecting unit 20 and provided to the processing unit 40.

Meanwhile, in a third state, third information relating to a position of the first pattern, for example the position of a first point on the first surface 50a, is obtained. In the third state, the substrate 50 may have warpage which is different from the first warpage. In a fourth state, fourth information relating to a position of the second pattern, for example the position of a second point on the first surface 50a,) is obtained. In the fourth state, the substrate 50 has warpage which is different from the second warpage. For example, the warpage in the fourth state may be substantially the same as the warpage in the third state. The third information and the fourth information are obtained by, for example, the first pattern detecting unit 31. This information may also be obtained by any other embodiments of a pattern accuracy detecting apparatus 110. The third information and the fourth information are provided to the processing unit 40.

Based on the first information (information relating to the first warpage in the first state), the second information (information relating to the second warpage in the second state), the third information (information relating to a position of the first pattern in the third state of warpage different from the first warpage), the fourth information (information relating to a position of the second pattern in the fourth state of warpage), the processing unit 40 derives a value indicating a difference between the position of the first point and the position of the second point in the second state of the second warpage. This value indicates alignment of the first pattern with the second pattern.

The processing unit 40 derives alignment error of the two patterns as a value which is based on the first warpage and the second warpage. For example, even when the two patterns cannot be directly compared to each other, the alignment error of the two patterns is obtained. Information (data) relating to each position of the two patterns is corrected on the basis of information indicating the two warpages. Accordingly, the alignment error of the two patterns can be derived with high accuracy.

For example, based on the detected alignment error, processing of subsequent substrates (for example, substrates in subsequently processed lots, or the like) can be adjusted to reduce the alignment error. Accordingly, manufacturing yield can be improved, size of elements on a semiconductor device can be minimized, and storage density of a storage device can be improved, among other things.

As illustrated in FIG. 1, the pattern accuracy detecting apparatus 110 may further include a first pattern detecting unit position detecting unit 35. The pattern accuracy detecting apparatus 110 may further include a second pattern detecting unit 32. The pattern accuracy detecting apparatus 110 may further include a second pattern detecting unit position detecting unit 36. The pattern accuracy detecting apparatus 110 may further include a temperature distribution measuring unit 38, which will be described later.

The pattern accuracy detecting apparatus 110 may be used with, for example, an exposing device 71 (irradiating device), a processing device 72 (etching device), a film forming device 73, and the like. The exposing device 71 and the processing device 72 are included in a processing unit 70, which may be a lithography device or apparatus. For example, a processing system 210 includes the pattern accuracy detecting apparatus 110 and the processing unit 70. A process in the processing device 72 includes, for example, at least one of a wet process and a dry process.

Hereinafter, an example of operation of the pattern accuracy detecting apparatus 110 will be described.

FIG. 2A to FIG. 2H are schematic sectional views exemplifying the operation of the pattern accuracy detecting apparatus according to the first embodiment.

Figure 2A:
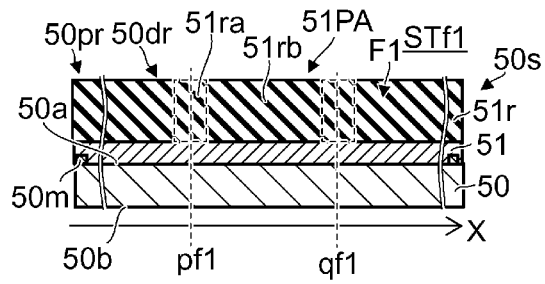
FIG. 2A to FIG. 2H are schematic sectional views exemplifying operation of the pattern accuracy detecting apparatus according to the first embodiment.

FIG. 2A exemplifies a state when the wafer 50s is disposed on the stage of the irradiating device (for example, exposing device 71). The first surface 50a of the substrate 50 includes a peripheral region 50pr and a functional, or device, region 50dr. The peripheral region 50pr is outside of the functional region 50dr, along a periphery of the wafer 50s. An alignment mark 50m may be disposed on or in the peripheral region 50pr.

A first process layer 51 is disposed on the first surface 50a of the substrate 50. The first process layer 51 is, for example, any one of a conductive layer (metal layer, semiconductor layer, or the like) and an insulating layer. The first process layer 51 may include a plurality of stacked layers.

A first resist film 51r is disposed on the first process layer 51. In the wafer 50s, stress and warpage may be generated by at least any one of the substrate 50, the first process layer 51, and the first resist film 51r. Even when the wafer 50s includes warpage, in a state in which the wafer 50s is adhered to the stage of the irradiating device (exposing device 71), the wafer 50s is, for example, substantially flat. This state may be a third state STf1. The third state STf1 is, for example, a first flat state.

The irradiating device (exposing device 71) emits an electromagnetic ray (light or other electromagnetic radiation) to a part of the first resist film 51r. For example, the first resist film 51r includes a first region 51ra and a second region 51rb. In an exemplary process, the electromagnetic ray is applied to one of the first region 51ra and the second region 51rb, and the electromagnetic ray is not applied to the other. If the first resist film 51r is a positive resist, for example, light is applied to the first region 51ra, and is not applied to the second region 51rb. The first resist film 51r corresponds to a first film F1.

A pattern of the first region 51ra and the second region 51rb corresponds to a first pattern 51PA which is disposed on the first resist film 51r.

For example, a position pf1 of a part of the first region 51ra and a position qf1 of another part of the first region 51ra are set to a reference position of the first pattern 51PA disposed on the first resist film 51r, and may be used to indicate the position of the first pattern 51PA. These positions are, for example, a position along the X axis direction.

After irradiation, the wafer 50s is removed from the irradiating device (exposing device 71), and development of the first resist film 51r is performed, for example using the processing device 72.

Figure 2B:
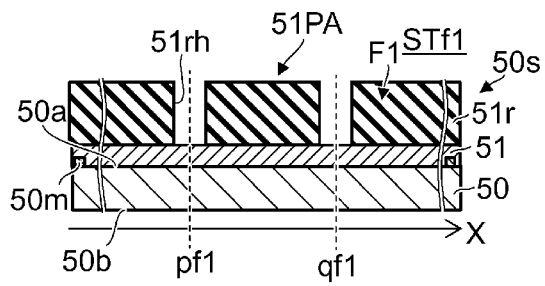
Figure 2C:
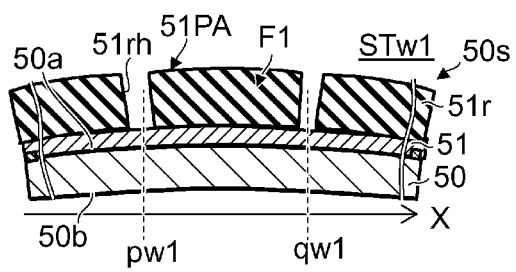

Accordingly, as illustrated in FIG. 2B, a first lithography process is performed in which an opening 51rh is formed in the first resist film 51r.

FIG. 2B illustrates a state in which the substrate 50 of the wafer 50s is removably adhered to a flat stage (stage 10, stage of exposing device 71, or the like, illustrated in FIG. 1). This state is referred to herein as the third state STf1. A size of the opening 51rh formed by the first lithography may not be matched with a size of the first region 51ra due to accuracy of the lithography process, but the position pf1 of the opening 51rh is substantially the same as the corresponding position of the first region 51ra. Similarly, the position qf1 is substantially the same as the corresponding position of the first region 51ra for forming the corresponding opening.

Afterward, the first pattern detecting unit 31 (refer to FIG. 1) may be used to detect the position (position pf1 and position qf1) of the opening 51rh. A detection result (data) becomes the third information.

As noted above, during pattern detection, the substrate 50 is supported by the supporting unit 10s (pin 10p). For example, the pin 10p is located at an upper position. In this state, the substrate 50 is not adhered to the stage (stage 10 illustrated in FIG. 1, or the like), stress is not substantially applied to the substrate 50 to make it flat, and so the wafer 50s may be warped during pattern detection. This state is referred to herein as the first state STw1, representing a first warpage of the wafer 50s, and the result of the pattern detection in state STw1 may be affected by the first warpage. To wit, the position pw1 of the opening 51rh detected by the pattern detecting unit 31 may be different from the position pf1 of the opening 51rh when formed in state STf1, and the position qw1 may likewise be different from position qf1.

Figure 2D:
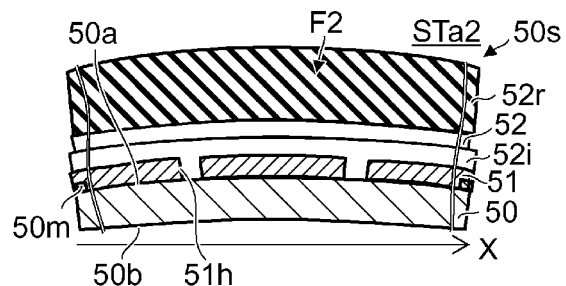

As illustrated in FIG. 2D, the first process layer 51 is processed using the first resist film 51r in which the opening 51rh is formed. For example, an etching process is performed on the first process target layer 51 using the first resist film 51r, patterned with openings 51rh, as a mask. The processing device 72 may be used to apply the pattern of the first resist film 51r to the first process layer 51. Accordingly, an opening 51h is formed in the first process target layer 51. The opening 51h corresponds to the opening unit 51rh of the first resist film 51r. After that, the first resist film 51r is removed.

The first surface 50a of the substrate 50 may be exposed in the opening 51h. An intermediate layer 52i is formed on the first process layer 51 using, for example, the film forming device 73. The intermediate layer 52i may have light-transmissive properties. The opening 51h is filled with the intermediate layer 52i. A second process layer 52 is formed on the intermediate layer 52i using, for example, the film forming device 73. The second process layer 52 may have light-shielding properties. In such cases, the first pattern 51PA of the first process layer 51 cannot be directly observed through the second process layer 52. In the embodiment, the second process layer 52 may be located on the functional region 50dr of the substrate 50, and not on the peripheral region 50pr. In this case, the alignment mark 50m located on the peripheral region 50pr may still be observable even after the second process layer 52 is formed. A second resist film 52r is formed on the second process layer 52.

Figure 2E:
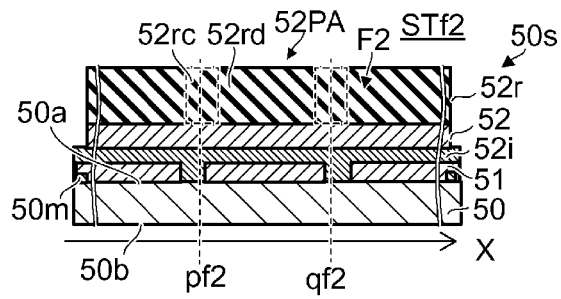

FIG. 2E illustrates a state when the wafer 50s is disposed on a stage of the irradiating device (exposing device 71). As noted above, in a state in which the wafer 50s is removably adhered to the stage of the irradiating device (exposing device 71), the wafer 50s is substantially flat. This state is referred to herein as the fourth state STf2. The fourth state STf2 is, for example, a second flat state.

As illustrated in FIG. 2E, the irradiating device (exposing device 71) emits an electromagnetic ray to a part of the second resist film 52r. For example, the second resist film 52r includes a third region 52rc and a fourth region 52rd. The electromagnetic ray is applied to one of the third region 52rc and the fourth region 52rd and not to the other. If the second resist film 52r is a positive resist, for example, light is applied to the third region 52rc and not to the fourth region 52rd. A position at which the electromagnetic ray is applied to the second resist film 52r may be controlled by, for example, the alignment mark 50m disposed on the peripheral region 50pr. The second resist film 52r corresponds to a second film F2.

A pattern of the third region 52rc and the fourth region 52rd corresponds to a second pattern 52PA disposed in the second resist film 52r.

For example, a position pf2 of a part of the third region 52rc and a position qf2 of another part of the third region 52rc become a reference position of the second pattern 52PA indicating the position of the second pattern 52PA. These positions are, for example, a position along the X axis direction.

As illustrated in FIG. 2E, although alignment of the patterns 51PA and 52PA might be desired, the position pf2 is different from the position pf1, and the position qf2 is different from the position qf1 (refer to FIG. 2A), due to deformation of the wafer 50s during processing, characteristic fluctuation of the exposing device 71, or the like.

The wafer 50s is removed from the exposing device 71, and development of the second resist film 52r is performed, for example using the processing device 72.

Figure 2F:
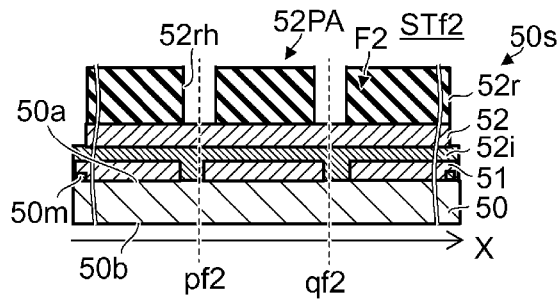

Accordingly, as illustrated in FIG. 2F, an opening 52rh is formed in the second resist film 52r by a second lithography process. The wafer 50s is in the fourth state STf2 in FIG. 2F.

A state of warpage of the substrate 50 in the fourth state STf2 is substantially same as a state of warpage of the substrate 50 in the third state STf1. The substrate 50 may not be completely flat in the third state STf1 and the fourth state STf2. A size of the opening 52rh formed by the second lithography, may be different from a size of the third region 52rc due to the accuracy of the lithography process. However, the position of the opening 52rh is substantially the same as the corresponding position pf2 of the third region 52rc, and likewise for the position qf2.

Afterward, the positions of the openings 52rh at position pf2 and position qf2 are detected by the first pattern detecting unit 31 (refer to FIG. 1).

Figure 2G:
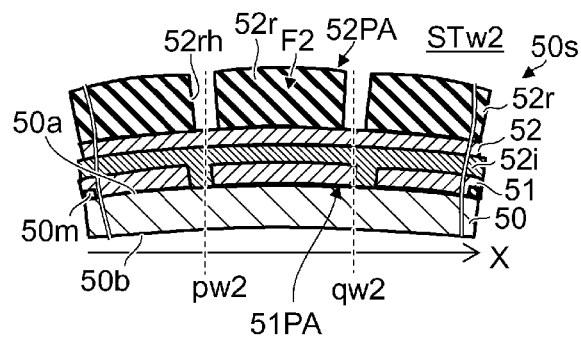

FIG. 2G illustrates a state in which the substrate 50 of the wafer 50s is supported by the supporting unit 10s and pin 10p during pattern detection. As noted above, the substrate 50 is not removably adhered to the stage (stage 10 illustrated in FIG. 1, or the like), so the wafer 50s may be warped. This state is referred to herein as STw2, and represents a second warpage of the wafer 50s. As noted above in connection with the first warpage, the second warpage affects the results of pattern detection. In the second state STw2, the second warpage of the substrate 50 is detected by the warpage detecting unit 20 (refer to FIG. 1). As above, the positions pw2 and qw2 of the openings 52rh are not exactly the same as the positions pf2 and qf2 of the third region 52rc due to the warpage. Moreover, the position pw2 is different from the position pw1 and the position qw2 is different from the position qw1.

Figure 2H:
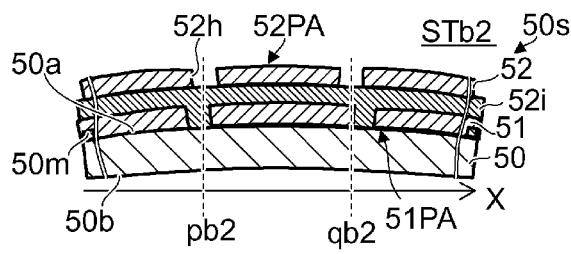

As illustrated in FIG. 2H, the second process layer 52 is processed using the second resist film 52r, in which the openingss 52rh are disposed, as a mask. For example, an etching process is performed on the second process layer 52, using, for example, the processing device 72. Accordingly, an opening 52h is formed in the second process layer 52. The opening 52h corresponds to the opening 52rh of the second resist film 52r. The second resist film 52r is then removed.

In FIG. 2G and FIG. 2H, if the second process layer 52 has light-shielding properties, the first pattern 51PA of the first process target layer 51 cannot be directly observed. Therefore, a difference between a reference position, for example the position pw2 and position qw2, in the state STw2 and the reference position, for example the position pw1 and position qw1, in the first state STw1 cannot be derived by a direct observation.

In the embodiment, based on warpage of a first warpage state such as the first state STw1, warpage of a second warpage state such as the state STw2, a position of the first pattern 51PA in the third state STf1, and a position of the second pattern 52PA in the fourth state STf2, a position difference between the first pattern 51PA and the second pattern 52PA in the second state is derived. From this, alignment error of the first pattern 51PA and the second pattern 52PA can be estimated.

The position relating to the first pattern 51PA (positions pf1 and qf1), and the position relating to the second pattern 52PA (positions pf2 and qf2) are obtained with the substrate in similar topological states, in this case both states where the substrate is substantially flat. Meanwhile, a difference between the first warpage (first state STw1) and the second warpage (second state STw2) is obtained (refer to FIG. 2C and FIG. 2G). Based on the warpage difference, when the substrate is in the second state STw2, a difference between the position (position pf1 and position qf1) relating to the first pattern 51PA and the position (position pf2 and position qf2) relating to the second pattern 52PA can be corrected. While the positions are detected in the various states of warpage, an accurate alignment error based on similar states of warpage or flatness is desired. By measuring the pattern positions with the substrate in similar topological states, and by detecting the first and second warpage states, and the differences between the two states, an accurate alignment error can be obtained.

For example, regarding the first pattern 51PA, a first distance (distance along X axis direction) between the position pf1 and the position qf1 is obtained. Meanwhile, regarding the second pattern 52PA, and a second distance (for example a distance along the X-axis direction) between the position pf2 and the position qf2 is obtained. If the warpage is the same in the first state STw1 and the second state STw2, the alignment error is directly related to a difference between the first distance and the second distance. If the warpage of the first state STw1 and the warpage of the second state STw2 are different, the difference between the first distance and the second distance is corrected according to the difference in warpage.

Figure 3:
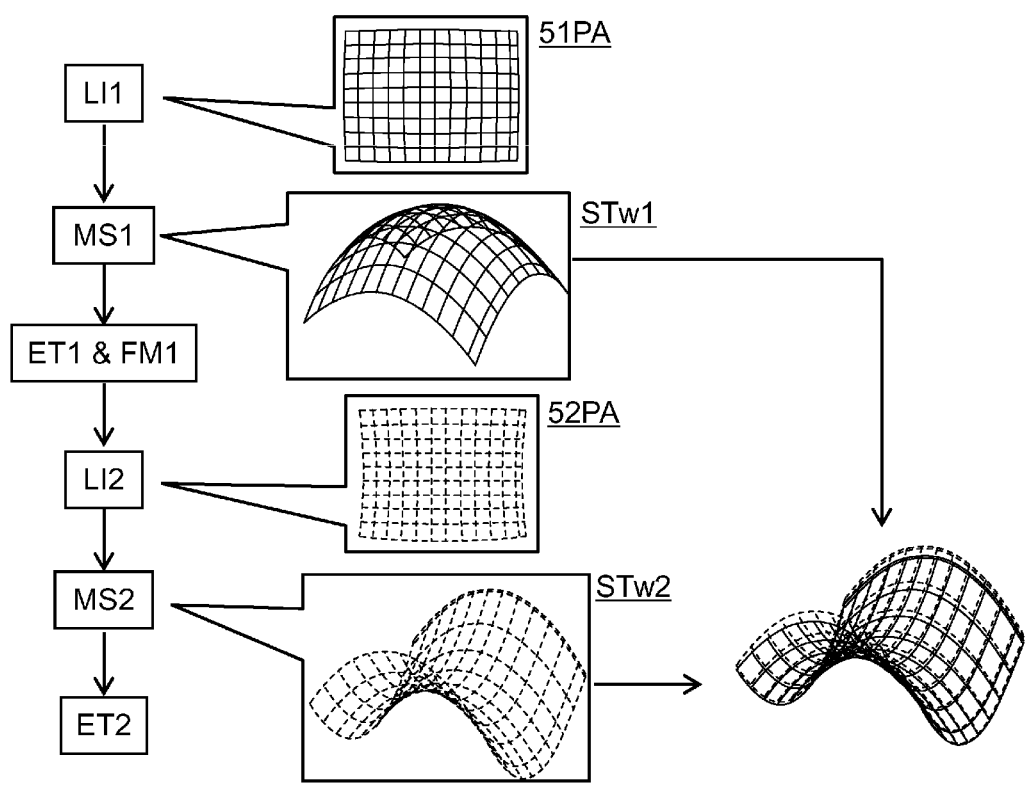
FIG. 3 is a schematic view exemplifying the operation of the pattern accuracy detecting apparatus according to the first embodiment.

FIG. 3 is a schematic view exemplifying an operation of the pattern accuracy detecting apparatus according to the first embodiment.

As illustrated in FIG. 3, the first lithography (Step LI1) is performed. Accordingly, the first pattern 51PA is formed on the first resist film 51r (first film F1). Also, in the third state STf1, regarding the first pattern 51PA, a position (position pf1, position qf1, and the like) of a pattern is obtained. Derivation of the position is performed by, for example, the first pattern detecting unit 31 (refer to FIG. 1), or the like.

In the first warpage state (first state STw1), the warpage of the substrate 50 (wafer 50s) is obtained (Step MS1). The derivation of the warpage is performed by the warpage detecting unit 20.

In the process illustrated in FIG. 3, processing (for example, first etching) of the first process layer 51 is next performed using the first resist film 51r (Step ET1), for example using the processing device 72. Further, for example, the intermediate layer 52i, the second process layer 52, and the second resist film 52r are formed (Step FM1), for example using the film forming device 73.

The second lithography (Step LI2) is performed. Accordingly, the second pattern 52PA is formed in the second resist film 52r (second film F2). In the fourth state STf2, regarding the second pattern 52PA, the position (position pf2, position qf2, and the like) of the pattern is obtained. The derivation of the position is performed by, for example, the first pattern detecting unit 31 (refer to FIG. 1), or the like.

In the second warpage state (state STw2), the warpage of the substrate 50 (wafer 50s) is obtained (Step MS2). The derivation of the warpage is performed by the warpage detecting unit 20.

Processing (for example, second etching) of the second process layer 52 is performed using the second resist film 52r (Step ET2) and the processing device 72.

In the embodiment, a difference between the first warpage state (first state STw1) and the second warpage state (state STw2) is calculated. According to the difference, a difference between a position (position pf1, position qf1, and the like) of the first pattern 51PA and a position (position pf2, position qf2, and the like) of the second pattern 52PA is corrected. Processing for determining the correction is performed by the processing unit 40.

Therefore, in the pattern accuracy detecting apparatus 110 according to the embodiment, the warpage detecting unit 20 detects, for example, the first warpage in the first state STw1 of the substrate 50 (wafer 50s) and the second warpage in the second state STw2 of the substrate 50 (wafer 50s). In the first state STw1, the first film F1 which includes the first pattern 51PA is disposed on the first surface 50a of the substrate 50. In the second state STw2, the second film F2 which includes the second pattern 52PA is disposed on the first surface 50a. In the example described above, the first film F1 is the first resist film 51r, and the second film F2 is the second resist film 52r.

In the example, in the first state STw1, the first process layer 51 is formed on the first surface 50a. The first film F1 is formed on the first process layer 51. In the example, in the second state STw2, the second process layer 52 is formed on at least a part of the first process layer 51. The second film F2 is formed on the second process layer 52.

In the embodiment, based on information (first information and second information) relating to two warpage states and information (third information and fourth information) relating to the position of two patterns, the processing unit 40 derives a value in accordance with a difference between the position of the first pattern 51PA and the position of the second pattern 52PA in the second state of the second warpage. The position of the first pattern 51PA and the position of the second pattern 52PA are related to positions on the first surface 50a.

Accordingly, even when the first pattern 51PA and the second pattern 52PA cannot be directly compared to each other, a difference of the positions of the patterns, which may be an alignment error, can be accurately calculated. In conventional processes using the alignment mark 50m to determine alignment error, effects of substrate warpage on pattern alignment cannot be accurately determined. Using the methods and apparatus described herein, however, effects of substrate warpage on pattern alignment can be accurately determined, allowing high accuracy patterning of functional elements in semiconductor devices, leading to size reduction with high manufacturing yield and device reliability.

FIG. 4A to FIG. 4D are schematic views exemplifying detection of the substrate pattern accuracy.

As illustrated in FIG. 4A, the second process layer may have light-shielding properties, so the first pattern 51PA and the second pattern 52PA cannot be optically and directly compared to each other. In the embodiment, based on the warpage in the first state STw1 and the warpage in the second state STw2, a difference between the position of the first pattern 51PA and the position of the second pattern 52PA can be corrected. Accordingly, the alignment error between the first pattern 51PA and the second pattern 52PA can be calculated with high accuracy.

As illustrated in FIG. 4B, the second process layer 52 may have light-transmissive properties, and the first pattern 51PA and the second pattern 52PA can be optically and directly compared to each other. However, optical comparison relies on a consistent and/or predictable distance t1 between the first surface 50a and a lower surface of the second resist film 52r to interpret the optical inspection. If the distance t1 is variable, calculation of alignment error is less accurate due, for example, to refractive effects of the varying thickness t1. For example, a phase of measuring light Le for detecting position of the pattern changes according to the distance t1. Therefore, a signal intensity of the measuring light Le becomes variable, and measurement accuracy is compromised. In contrast, in methods described herein, based on the warpage in the first state STw1 and the second state STw2, the difference between the position of the first pattern 51PA and the position of the second pattern 52PA can be corrected, without measurement error from the varying thickness t1. Accordingly, the alignment error can be calculated with high accuracy.

Figure 4C:
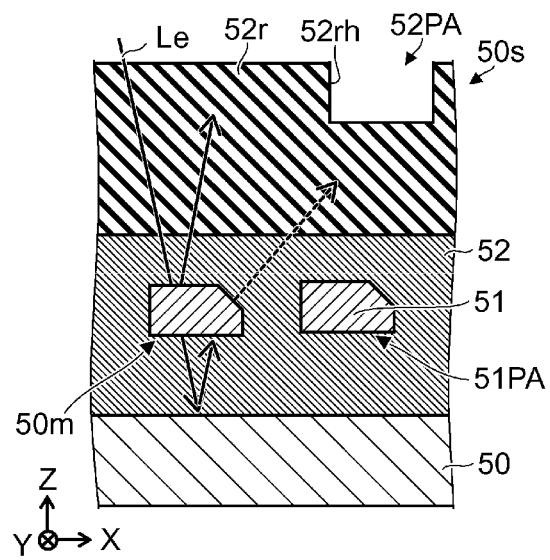

As illustrated in FIG. 4C, the first pattern 51PA of the first process layer 51 may be asymmetrically formed. If optical techniques are used to detect the position of the first pattern 51PA, non-uniform reflective surfaces may introduce measurement error. For example, a signal peak of the measuring light Le may be shifted by angled reflective surfaces, reducing accuracy of the result. The methods described herein do not depend on uniform patterning and reflective surfaces. Based on the warpage in the first state STw1 and second state STw2, the detected alignment error can be corrected without influence of reflective effects on the measuring light Le. Accordingly, alignment error can be obtained with high accuracy.

Figure 4D:
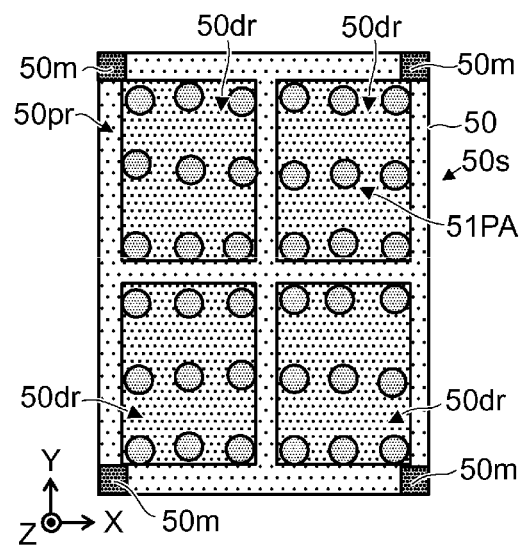

FIG. 4D illustrates a reference example in which alignment error is obtained using the alignment mark 50m in the peripheral region 50pr. In a typical process, a dedicated mark pattern (for example, the alignment mark 50m) is formed by applying a layer, and the mark pattern is optically measured to determine alignment error. In such a method, alignment error of the pattern in the functional region 50dr cannot be measured with any accuracy. Such methods add further complexity due to inconsistent use and application of alignment marks in different processes. Layer stacking processes can cover prior marks, requiring new marks to be applied, frequently in inconsistent positions, and directed self-assembly processes can interfere with previously applied marks.

Using the methods described herein, a three-dimensional position of the substrate 50 is measured. That is, the warpage detecting unit 20 detects the warpage of the substrate 50. Based on a detecting result of the warpage, the alignment error is calculated. Accordingly, the alignment error in any suitable region (for example, the functional region 50*dr*) of the substrate 50 can be detected with high accuracy.

FIG. 5A to FIG. 5D are schematic views exemplifying detection of the substrate pattern accuracy.

Figure 5A:
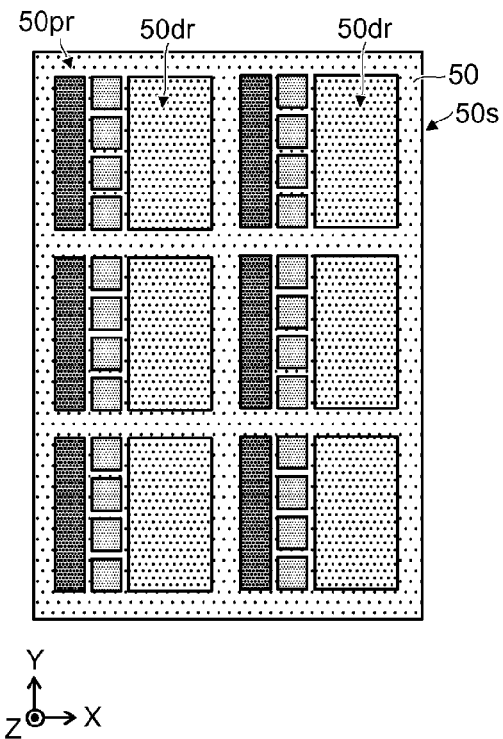
FIG. 5A to FIG. 5D are schematic views exemplifying the detection of the accuracy of the substrate pattern.

As illustrated in FIG. 5A, in the substrate 50 (wafer 50*s*), for example, a plurality of functional regions 50*dr* are included. The peripheral region 50*pr* is disposed near the functional region 50*dr*.

Figure 5B:
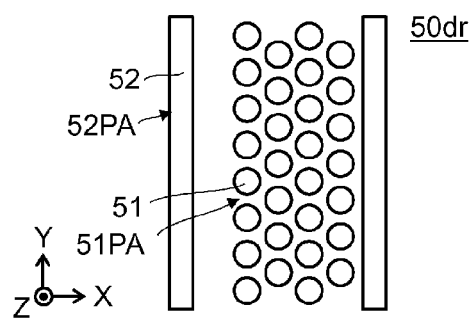

As illustrated in FIG. 5B, the first process layer and the second process layer 52 are formed in the functional region 50*dr*. In this example, the first process layer 51 includes a hole pattern (first pattern 51PA), and the second process layer 52 includes a line pattern (second pattern 52PA). The first pattern 51PA is, for example, a contact pattern. In this example, the second pattern 52PA is shifted in the X-direction with respect to the first pattern 51PA. The first and second patterns 51PA and 52PA may be shifted in the X-direction with respect to the design position, as shown by broken lines in FIGS. 5C and 5D.

Figure 5C:
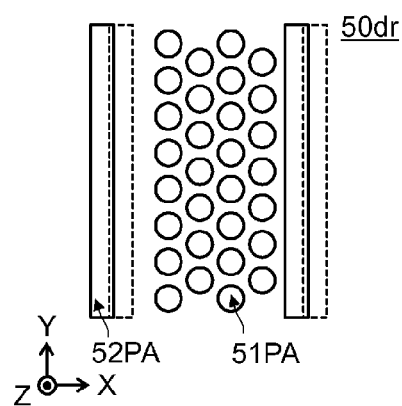
Figure 5D:
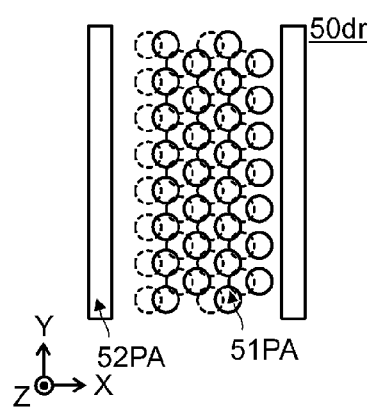

Using conventional methods, it is not easy to determine whether alignment error in the two patterns disposed on the functional region 50*dr* is due to the error of FIG. 5C or the error of FIG. 5D. In contrast, using the pattern accuracy detecting apparatus 110 according to the embodiment, the alignment error of each of the two patterns in the functional region 50*dr* can be individually detected. Accordingly, it is possible to determine whether the alignment error in the two patterns disposed on the functional region 50*dr* is due to the error of FIG. 5C or FIG. 5D, or a combination of the two.

In the embodiment, in detection of the warpage of the substrate 50, light (at least any one of the light 21L and the light 22L) is applied to substantially the entire surface of the substrate 50 (refer to FIG. 1). Accordingly, the warpage of the entire substrate 50 is detected in a single exposure. Additionally, when detecting of the warpage of the substrate 50, light (at least any one of light 21L and light 22L) can be applied to a part of the substrate 50, and a position along the Z axis direction of the part of the substrate 50 may be detected. As such, detection of a part of the substrate may be performed.

In an example illustrated in FIG. 1, the substrate is disposed on the stage 10. At this time, the substrate 50 is, for example, disposed substantially along an XY plane. When the substrate 50 includes warpage, a z-axis position of the center of the substrate 50 may be different from that of an edge portion of the substrate 50. When the substrate 50 is warped, the first surface 50*a* and the second surface 50*b* include a displacement in accordance with the warpage. The displacement of the second surface 50*b* substantially corresponds to the displacement of the first surface 50*a*.

In the embodiment, at the time of detecting the warpage of the substrate 50, the wafer 50*s* (substrate 50) may be supported so that the first surface 50*a* of the wafer 50*s* (substrate 50) is oriented along a direction of gravity, for example with a line perpendicular to the substrate 50*a* oriented along the direction of gravity. The supporting unit 10*s* may support (or hold) one side of the substrate 50.

In the embodiment, the stage position detecting unit 11 (refer to FIG. 1) detects the position of the stage 10 by at least any one of an optical, electrical, and electromagnetic method. The stage position detecting unit may include, for example, a Doppler interferometer. The stage position detecting unit 11 may detect the position of the stage 10 by, for example, optically detecting a position of a mark disposed on the upper surface 10*a* of the stage 10, or by detecting a state of the stage moving unit 11*dr*.

In the embodiment, as exemplified in FIG. 1, at least one of the first database 41 and the second database is included in the processing unit 40. In the embodiment, the database may be located at a position different from a position where the processing unit 40 is located. Communication between the database and the processing unit 40 may be performed by any suitable wired or wireless method.

The chamber 10*c* may be located at a position different from a position where the processing unit 40 is depicted in FIG. 1. Communication of data between various devices (warpage detecting unit 20, stage moving unit 11*dr*, stage position detecting unit 11, first pattern detecting unit 31, and the like) disposed inside the chamber 10*c*, and the processing unit 40 may be performed by any suitable wired or wireless method.

In the example illustrated in FIG. 1, first surface shape information obtained by the first surface shape measuring unit 21 is supplied to the first database 41 through a transmission medium 21*s*. Second surface shape information obtained by the second surface shape measuring unit 22 is supplied to the first database 41 through a transmission medium 22*s*. Information relating to the position of the stage 10 detected by the stage position detecting unit 11 is supplied to the first database 41 through a transmission medium 11*s*. Information relating to the position of a pattern detected by the first pattern detecting unit 31 is supplied to the first database 41 through a transmission medium 31*s*. Information (data) supplied to the first database 41 is supplied to the processing unit 40 through a transmission medium 41*s*. A process result (data) in the processing unit 40 is supplied to the second database 42 through a transmission medium 42*s*.

The first pattern detecting unit position detecting unit 35 may be disposed on the pattern accuracy detecting apparatus 110. The first pattern detecting unit position detecting unit 35 detects a position of the first pattern detecting unit 31. The position includes, for example, a position along the X-Y plane. The position may include a position along the Z axis direction. The first pattern detecting unit position detecting unit 35 detects the position of the first pattern detecting unit 31 with high accuracy. Accordingly, the first pattern detecting unit is capable of detecting a position of the pattern disposed on the first surface 50*a* of the substrate 50 with high accuracy.

For example, the first pattern detecting unit position detecting unit 35 is capable of monitoring the position of the first pattern detecting unit 31. The position of the first pattern detecting unit 31 may be changed due to influence of environmental factors such as temperature, or by a driving unit. When the position of the first pattern detecting unit 31 is monitored by the first pattern detecting unit position detecting unit 35, the change can be observed, and imaging accuracy improved.

The second pattern detecting unit 32 may be disposed on the pattern accuracy detecting apparatus 110. For example, a mark may be disposed on the second surface 50*b* of the substrate 50 (rear surface). The second pattern detecting unit 32 detects the mark. For example, an original point is determined at the time of calculating the warpage. The original point may be determined on the basis of, for example, the mark provided on a rear surface. A position of the mark provided on the rear surface can be detected by the second pattern detecting unit 32. For example, based on the mark provided on a rear surface as a reference point, three dimensional (warpage) position information of the substrate 50 is calculated, resulting in improved accuracy.

The second pattern detecting unit position detecting unit 36 may be further included in the pattern accuracy detecting apparatus 110. The second pattern detecting unit position detecting unit 36 detects a position of the second pattern detecting unit 32. The position may include a position along the X-Y plane. The position may include a position along the Z axis direction. The position of the second pattern detecting unit 32 is detected with high accuracy by the second pattern detecting unit position detecting unit 36. Accordingly, the position of the pattern disposed on the second surface 50b of the substrate 50 can be detected with high accuracy by the second pattern detecting unit 32.

The position of the second pattern detecting unit 32 is monitored by the second pattern detecting unit position detecting unit 36. For example, the position of the second pattern detecting unit 32 may be changed due to environmental factors such as temperature, or by a driving unit. When the position of the second pattern detecting unit 32 is monitored by the second pattern detecting unit position detecting unit 36, the change can be observed and imaging accuracy can be improved.

Data detected by the first pattern detecting unit position detecting unit 35 is supplied to, for example, the first database 41 through the transmission medium 35s. Data detected by the second pattern detecting unit 32 is supplied to, for example, the first database 41 through the transmission medium 32s. Data detected by the second pattern detecting unit position detecting unit 36 is supplied to, for example, the first database 41 through the transmission medium 36s.

The temperature distribution measuring unit 38 may be further included on the pattern accuracy detecting apparatus 110. The temperature distribution measuring unit 36 measures a temperature distribution of the substrate 50, for example along the first surface 50a. The temperature distribution measuring unit 38 may be an infrared sensor such as a pyrometer or infrared camera. Data detected by the temperature distribution measuring unit 38 is supplied to, for example, the first database 41 through the transmission medium 38s.

The substrate 50 may be warped due to temperature gradients in the substrate 50. For example, there is a predetermined relationship between the temperature distribution and the warpage, so warpage due to the temperature distribution detected by the temperature distribution measuring unit 38 can be estimated. The estimation is performed by, for example, the processing unit 40. In the processing unit 40, for example, position information obtained by a pattern detecting unit (first pattern detecting unit 31, second pattern detecting unit 32, and the like) may be corrected using the temperature distribution detected by the temperature distribution measuring unit 38. Accordingly, even when the substrate has temperature gradients, the influence thereof on warpage can be removed for improved accuracy. Measuring time can also be reduced. For example, measurement does not have to wait until the temperature of the substrate 50 is made uniform. When temperature of the substrate 50 must be regulated for accurate measurement, measuring time is longer. Measuring and removing the effect of temperature gradients mathematically reduces measuring time.

In the processing unit 40, for example, the warpage of the substrate 50 (first warpage in first state ST1, the second warpage in the second state ST2, and the like), which is obtained by the warpage detecting unit 20 (first surface shape measuring unit 21, second surface shape measuring unit 22, and the like), may be corrected on the basis of the temperature distribution of the substrate 50. Accordingly, a high accuracy is obtained and measuring time can be shortened.

In FIG. 2A to FIG. 2H, and FIG. 3, the first pattern 51PA is a pattern of the first resist film 51r, and the second pattern 52PA is a pattern of the second resist film 52r. That is, the first film F1 is the first resist film 51r, and the second film F2 is the second resist film 52r.

Hereinafter, another example of the operation of the pattern accuracy detecting apparatus 110 will be described. In the example hereinafter, the first pattern 51PA is a pattern of the first process layer 51, the second pattern 52PA is a pattern of the second resist film 52r. That is, the first film F1 is the first process layer 51, and the second film F2 is the second resist film 52r.

FIG. 6A to FIG. 6H are schematic sectional views exemplifying another operation of the pattern accuracy detecting apparatus according to the first embodiment.

Figure 6A:
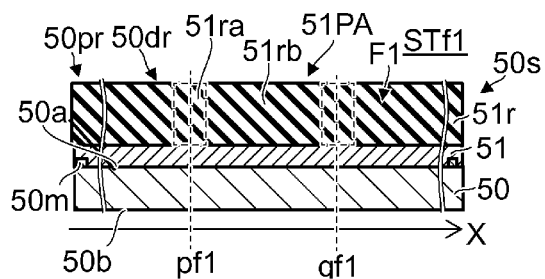
FIG. 6A to FIG. 6H are schematic sectional views exemplifying another operation of the pattern accuracy detecting apparatus according to the first embodiment.

In FIG. 6A, detailed description same as that of FIG. 2A will be omitted. The wafer 50s is disposed outside the irradiating device (exposing device 71), and development of the first resist film 51r is performed. Accordingly, the opening 51rh (refer to FIG. 2B) is provided on the first resist film 51r. Therefore, the first lithography is performed. Further, the first process layer 51 is processed using the first resist film 51r as a mask.

Figure 6B:
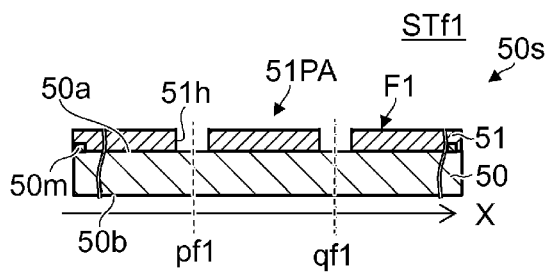

Accordingly, as illustrated in FIG. 6B, the opening 51h is formed in the first process layer 51. The opening 51h corresponds to the opening 51rh of the first resist film 51r. After that, the first resist film 51r is removed.

FIG. 6B illustrates a state (for example, the third state STf1) in which the substrate 50 of the wafer 50s is removably adhered to a flat stage (stage 10, stage of exposing device 71, or the like, illustrated in FIG. 1). In the state, for example, a position of the opening 51h (position pf1 and position qf1) is detected by the first pattern detecting unit 31 (refer to FIG. 1).

Figure 6C:
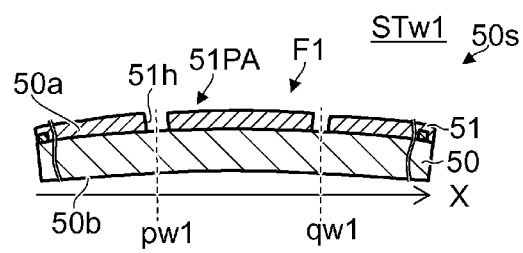
Figure 6D:
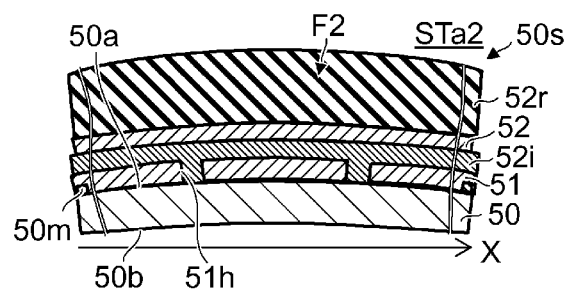
Figure 6E:
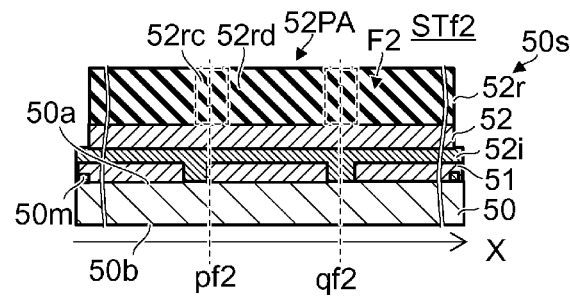
Figure 6F:
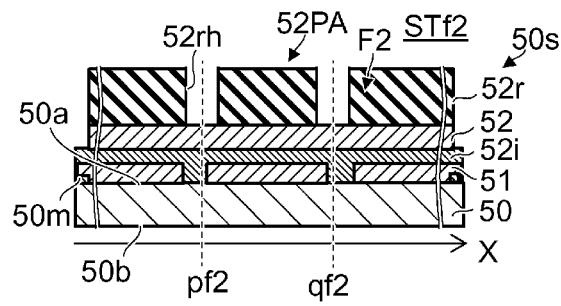
Figure 6G:
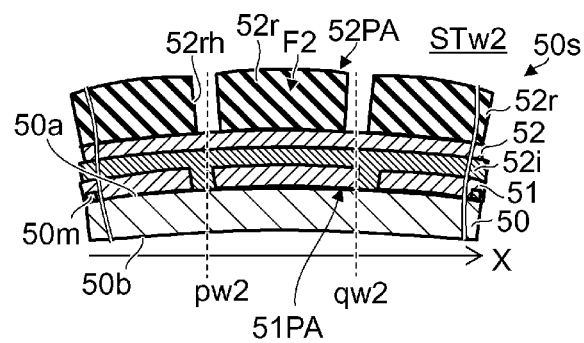
Figure 6H:
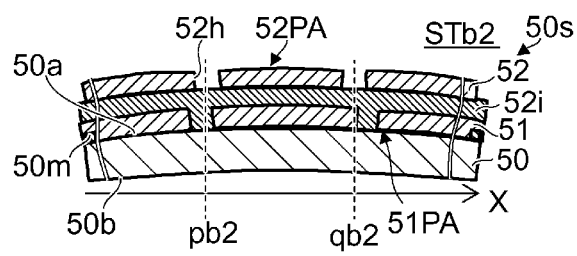

FIG. 6C illustrates a state in which the substrate 50 of the wafer 50s is supported by the supporting unit 10s (pin 10p). In the state, the substrate 50 is not removably adhered to the stage (stage 10, or the like illustrated in FIG. 1), and the substrate 50 is not made to be flat. Thus, the wafer 50s includes warpage and corresponds to the first state STw1.

In the first state STw1 (the state of first warpage), the warpage of the substrate 50 is detected by the warpage detecting unit 20 (refer to FIG. 1).

In FIG. 6D to FIG. 6H, detailed description same as those of FIG. 2D to FIG. 2H will be omitted. In the example illustrated in FIG. 6F, the opening 52rh is formed in the second resist film 52r. The position of the opening 52rh (position pf2 and position qf2) is detected by the first pattern detecting unit 31 (refer to FIG. 1). In the second state STw2 illustrated in FIG. 6G, the warpage of the substrate 50 is detected by the warpage detecting unit 20 (refer to FIG. 1).

In the example, the first film F1 is the first process layer 51 formed on the first surface 50a. In the second state STw2, the second process layer 52 is formed on at least a part of the first process layer 51. Also, the second film F2, corresponding to the second resist film 52r, is formed on the second process layer 52.

The warpage detecting unit 20 detects the first warpage in the first state STw1 of the substrate 50 and the second warpage in the second state STw2 of the substrate 50. In the first state STw1, the first film F1 (in this example, first process layer 51) in which the first pattern 51PA is included, is disposed on the first surface 50a of the substrate 50. In the second state STw2, the second film F2 (in this example, second resist film 52r) in which the second pattern 52PA is included, is disposed on the upper surface 50a.

Based on the first information to the fourth information, in the second state STw2, the processing unit derives a value in accordance with the difference between the position of the first pattern on the upper surface 50a and the position of the second pattern on the upper surface 50a. Accordingly, alignment error of the first and second patterns can be detected with high accuracy.

Hereinafter, another example of the operation of the pattern accuracy detecting apparatus 110 will be described. In the example described below, the first pattern 51PA is a pattern of the first resist film 51r, and the second pattern 52PA is a pattern of the second process layer 52. That is, the first film F1 is the first resist film 51r, the second film F2 is the second process target layer 52. This example demonstrates that alignment errors of films of varying composition can be determined using the methods described herein.

FIG. 7A to FIG. 7H are schematic sectional views exemplifying another operation of the pattern accuracy detecting apparatus according to the first embodiment.

Figure 7A:
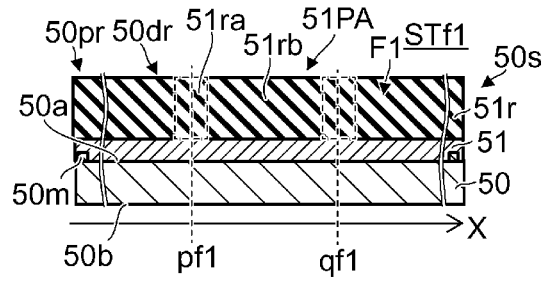
FIG. 7A to FIG. 7H are schematic sectional views exemplifying the other operation of the pattern accuracy detecting apparatus according to the first embodiment.
Figure 7B:
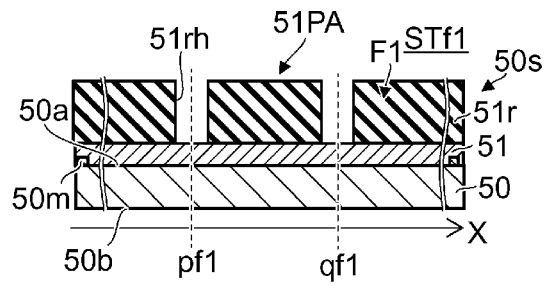

In FIG. 7A to FIG. 7F, detailed description same as those of FIG. 2A to FIG. 2F will be omitted. In this example, as illustrated in FIG. 7B, the substrate 50 of the wafer 50s is removably adhered to the flat stage (stage 10, stage of exposing device 71, or the like, illustrated in FIG. 1). In the state (for example, third state STf1), a position (position pf1 and position qf1) of the opening 51rh of the first resist film 51r (first film F1) is detected by the first pattern detecting unit 31 (refer to FIG. 1). Also, in the first state STw1 (a state in which the substrate 50 has the first warpage) illustrated in FIG. 7C, the warpage of the substrate 50 is detected by the warpage detecting unit 20 (refer to FIG. 1).

Figure 7C:
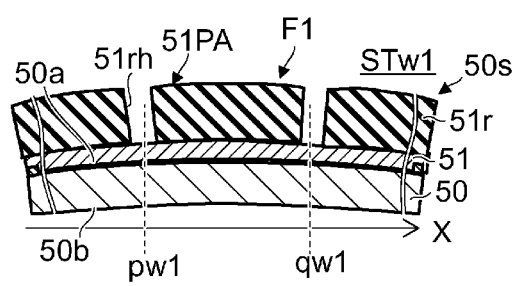
Figure 7D:
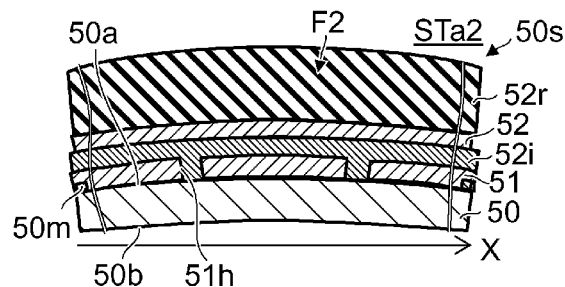
Figure 7E:
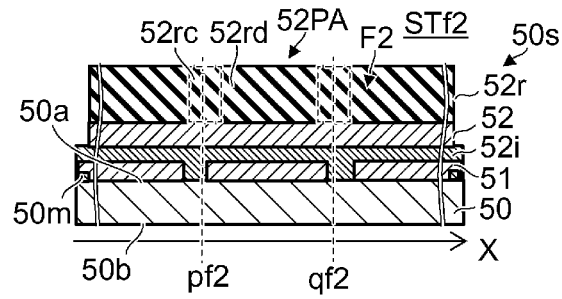
Figure 7F:
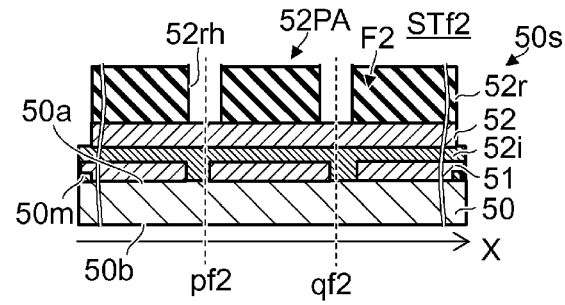
Figure 7G:
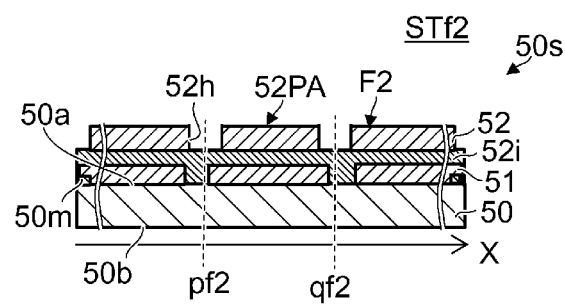

As illustrated in FIG. 7G, the second process layer is processed using the second resist film 52r as a mask. Accordingly, the opening 52h is formed in the second process layer 52. The second resist film 52r is removed. In the state (for example, fourth state STf2), for example, the position (position pf2 and position qf2) of the opening 52h is detected by the first pattern detecting unit 31 (refer to FIG. 1). The detected position represents the position of the second pattern 52PA.

Figure 7H:
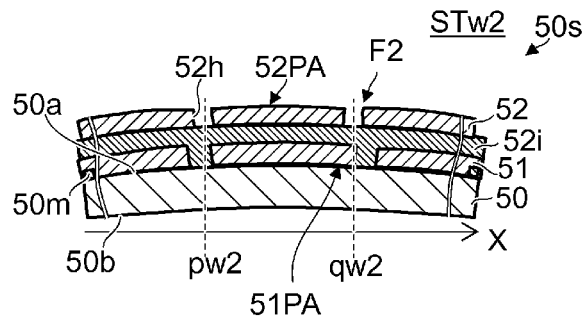

As illustrated in FIG. 7H, in the second state STw2 (a state in which the substrate 50 has the second warpage), the warpage of the substrate 50 is detected by the warpage detecting unit 20 (refer to FIG. 1).

Therefore, in this example, in the first state STw1, the first process layer 51 is located on the first surface 50a and the first film F1 (first resist film 51r) is located on the first process layer 51 (refer to FIG. 7C). The second film F2 is the second process layer 52 formed on the first process layer 51 after the first film F1 (first resist film 51r) is removed (refer to FIG. 7H).

In the example, based on the first information to the fourth information, in the second state STw2, the processing unit 40 derives a value in accordance with the difference between the position of the first pattern on the upper surface 50a and the position of the second pattern on the upper surface 50a. Accordingly, the alignment error can be detected with high accuracy.

Hereinafter, still another example of the operation of the pattern accuracy detecting apparatus 110 will be described. In the example hereinafter, the first pattern 51PA is a pattern of the first process target layer 51, and the second pattern 52PA is a pattern of the second process target layer 52. That is, the first film F1 is the first process target layer 51, and the second film F2 is the second process target layer 52.

FIG. 8A to FIG. 8H schematic sectional view exemplifying still another operation of the pattern accuracy detecting apparatus according to the first embodiment.

FIG. 8A to FIG. 8D are the same as FIG. 6A to FIG. 6D. FIG. 8E to FIG. 8H are the same as FIG. 7E to FIG. 7H. Thus, the additional elements of FIGS. 7E to 7H can be combined with the elements of FIGS. 8A to 8D.

Figure 8A:
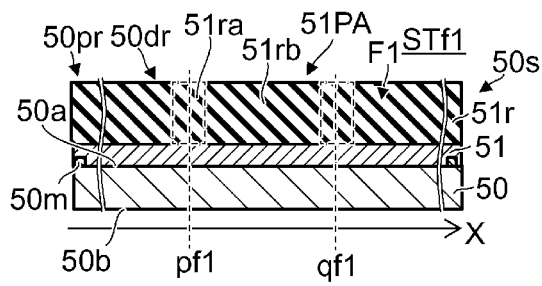
FIG. 8A to FIG. 8H are schematic sectional views exemplifying still another operation of the pattern accuracy detecting apparatus according to the first embodiment.
Figure 8B:
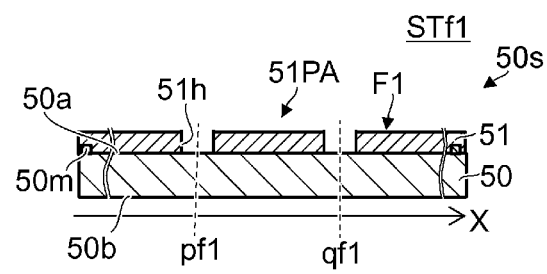
Figure 8C:
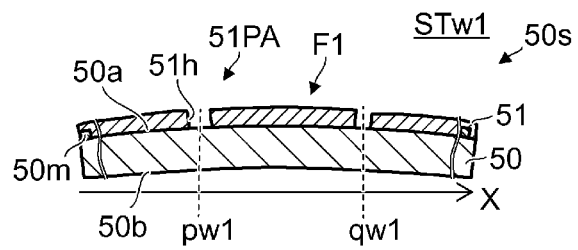
Figure 8D:
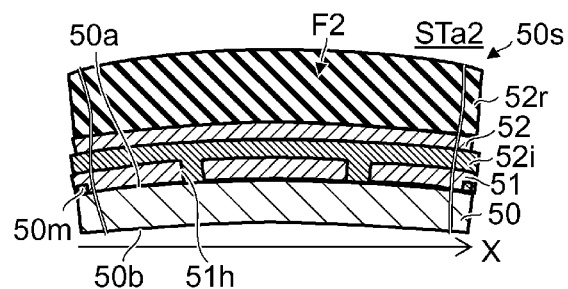
Figure 8E:
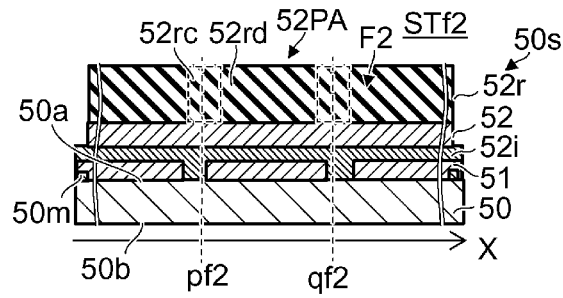
Figure 8F:
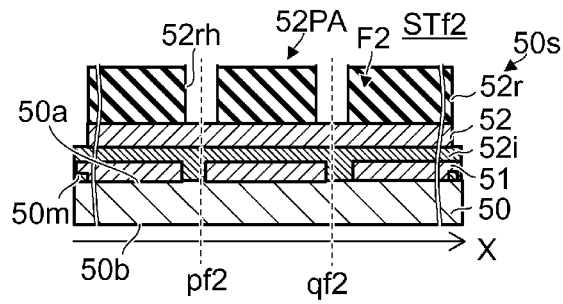

In the example, in the third state STf1 illustrated in FIG. 8B, the first pattern detecting unit 31 (refer to FIG. 1) detects the position (position pf1 and position qf1) of the opening 51h. In the first state STw1 (a state in which the substrate 50 has the first warpage) illustrated in FIG. 8C, the warpage detecting unit 20 (refer to FIG. 1) detects the warpage of the substrate 50.

Figure 8G:
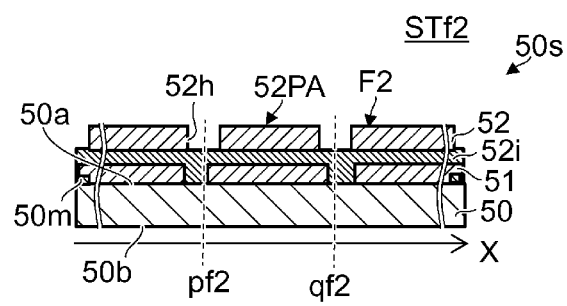
Figure 8H:
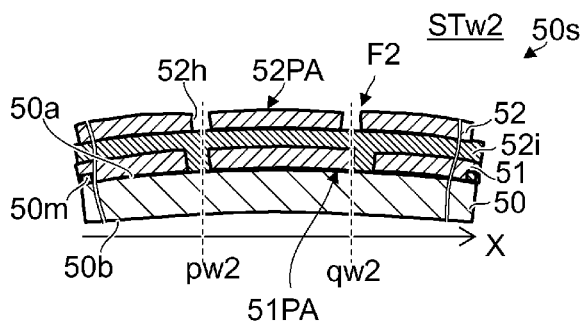

Further, in the fourth state STf2 illustrated in FIG. 8G, for example, the first pattern detecting unit 31 (refer to FIG. 1) detects the position (position pf2 and position qf2) of the opening 52h. As illustrated in FIG. 8H, in the state STw2 (a state in which the substrate 50 has the second warpage), the warpage detecting unit 20 (refer to FIG. 1) detects the warpage of the substrate 50.

In the example, the first film F1 is the first process layer 51 disposed on the first surface 50a. Also, at least a part of the second film F2 is disposed on at least a part of the first process layer 51.

Even in the example, based on the first information to the fourth information, in the state STw2, the processing unit 40 derives a value in accordance with the difference between the position of the first pattern and the second pattern on the upper surface 50a, allowing for detection of alignment error with high accuracy.

Second Embodiment

The pattern accuracy detecting apparatus 110 (refer to FIG. 1) according to the embodiment can be used to evaluate functioning of a device, or to calibrate a device.

Figure 9:
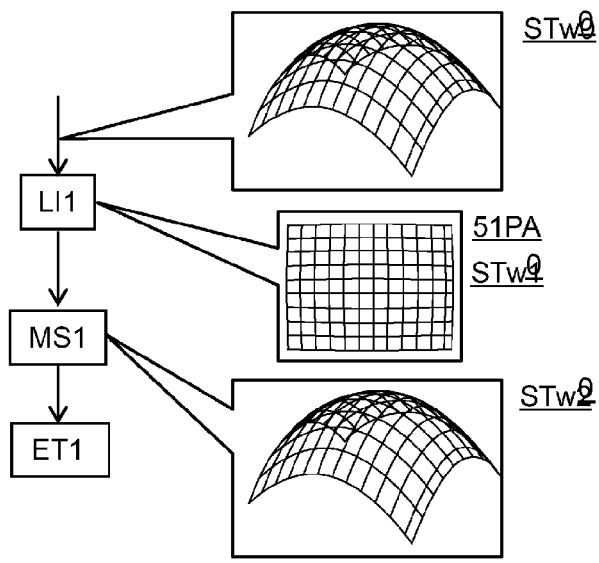
FIG. 9 is a schematic view exemplifying operation of a pattern accuracy detecting apparatus according to a second embodiment.

FIG. 9 is a schematic view exemplifying the operation of the pattern accuracy detecting apparatus 110 of FIG. 1 according to a second embodiment.

As illustrated in FIG. 9, the substrate 50 which includes warpage of an initial state STw00 is processed by the exposing device 71. The first film F1 is disposed on the first surface 50a of the substrate 50. The first film F1 is, for example, the first resist film 51r. From the exposing device 71, light corresponding to the first pattern 51PA is applied to the first film F1 (for example, Step LI1). At this time, the substrate 50 is removably adhered to a stage of the exposing device 71, or the like.

Let this state be the first state STw10. The warpage (first warpage) of the substrate 50 in the first state STw10 may be different from a state of the warpage of the substrate 50 in the initial state STw00. The substrate 50 in the first state STw10 is, for example, substantially flat. Therefore, the warpage (first warpage) of the substrate 50 in the first state STw10 is, for example, small. The warpage (first warpage) of the substrate 50 in the first state STw10 may be, for example, substantially zero. An intermediate film other than the first film F1 may be disposed in the substrate 50, and small warpage due to an influence of the intermediate film may also be present.

After light corresponding to the first pattern 51PA is applied from the exposing device 71 to the first film F1, the warpage detecting unit 20 detects the warpage (second warpage) of the substrate 50 (Step MS1). At the time of detecting the second warpage, the substrate 50 is supported by, for example, the three pins 10p (supporting unit 10s). In the state (second state STw20), stress from the outside is not substantially applied to the substrate 50. The warpage (first warpage) of the substrate 50 at the time of applying the light is different from the second warpage.

The processing unit 40 calculates an accuracy of the first pattern 51PA based on the first warpage (at the time of exposing) and the second warpage (when stress is not applied). For example, the first pattern 51PA is, for example, a grid pattern. After applying the light to the first pattern 51PA, for example, the first film F1 (for example, first resist film 51r) is developed. Accordingly, a pattern corresponding to the first pattern 51PA is formed in the first film F1.

Under consideration of an influence of warpage, based on a difference between the first warpage and the second warpage, when an accuracy of the first pattern 51PA is calculated, for example, performance of the exposing device 71 can be monitored. If the exposing device 71 is causing alignment error due to improper calibration, for example in focus, light direction, pattern mask position, or other factors, the methods and apparatus described herein can detect the alignment error repeatedly as changes are made to the exposing device 71 to improve the alignment error. Based on a calculated result of an accuracy of the first pattern 51PA, for example, calibration of the exposing device 71 may be performed. The second embodiment can be applied to, for example, management of the exposing device 71.

Third Embodiment

This embodiment relates to the processing system 210 (refer to FIG. 1). The processing system 210 includes the warpage detecting unit 20 and the processing unit 70 shown in FIG. 1. The processing system 210 may also include the processing unit 40. The processing unit 40 may further include the processing unit 70.

Figure 10:
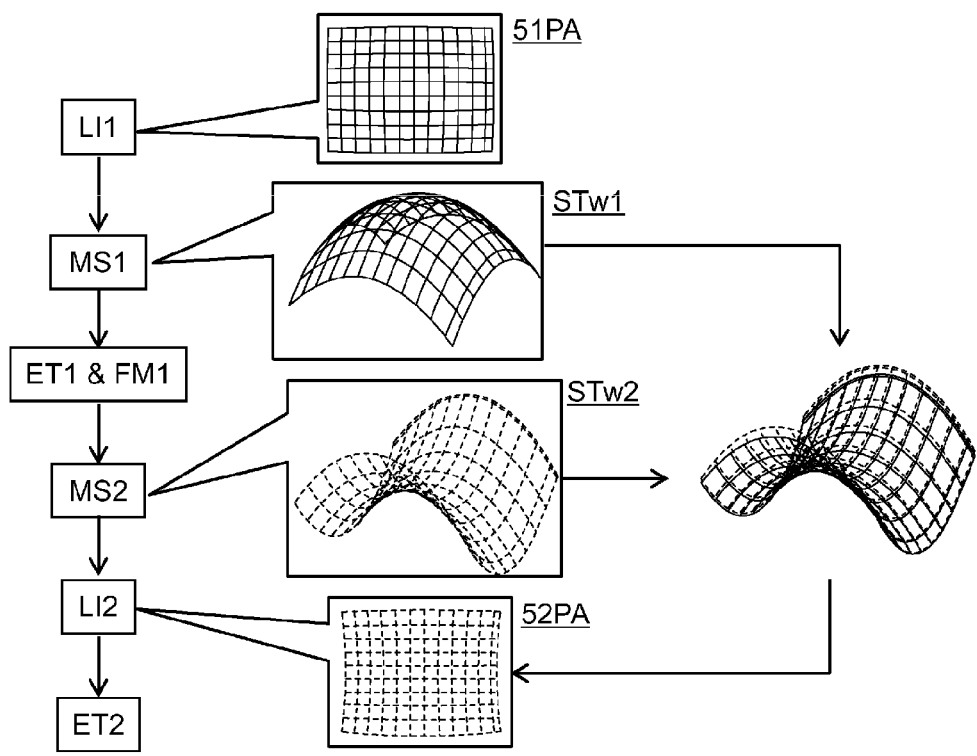
FIG. 10 is a schematic view exemplifying operation of a processing system according to a third embodiment.

FIG. 10 is a schematic view exemplifying an operation of the processing system according to the third embodiment.

As illustrated in FIG. 10, the first lithography (Step LI1) is performed. Accordingly, the first pattern 51PA is disposed on the first resist film 51r (first film F1). Also, regarding the first pattern 51PA, a position (position pf1, position qf1, or the like) of a pattern is obtained (for example, refer to FIG. 2B). The derivation of the position is performed by, for example, the first pattern detecting unit 31, or the like (refer to FIG. 1).

In the first warpage state (first state STw1), the warpage of the substrate 50 (wafer 50s) is obtained (Step MS1). Derivation of the warpage is performed by the warpage detecting unit 20.

For example, processing (for example, first etching) of the first process layer 51 is performed using the first resist film 51r (Step ET1) and the processing device 72. Further, for example, the intermediate layer 52i, the second process layer 52, and the second resist film 52r are formed (Step FM1).

In the second warpage state (state STw2), the warpage of the substrate 50 (wafer 50s) is obtained (Step MS2). The derivation of the warpage is performed by the warpage detecting unit 20. In the state STw2, the second film F2 (for example, second resist film 52r) is unpatterned.

The second lithography (Step LI2) is performed (for example, refer to FIG. 2E and FIG. 2F). At this time, based on information (data) relating to the warpage in the first state STw1 and information (data) relating to the second state STw2, a condition in the second lithography is adjusted. That is, a feed-forward is performed. For example, since the corrected pattern position resulting from the first lithography is known from the detected first pattern position, warpage state, etc., deviation from the design of the first lithography can be applied to adjust the second lithography. The second warpage of the wafer, with the unpatterned second film F2, is also useful in adjusting the second lithography since the detected second warpage indicates how the result of the second lithography will subsequently be detected.

Accordingly, the second pattern 52PA is formed in the second resist film 52r (second film F2). In the second pattern 52PA, the position (position pf2, position qf2, and the like) of the pattern is obtained. The derivation of the position is performed by, for example, the first pattern detecting unit 31 (refer to FIG. 1), or the like.

Afterwards, processing (for example, second etching) of the second process layer 52 is performed (Step ET2, for example, refer to FIG. 2H), for example, using the second resist film 52r and the processing device 72.

Figure 11A:
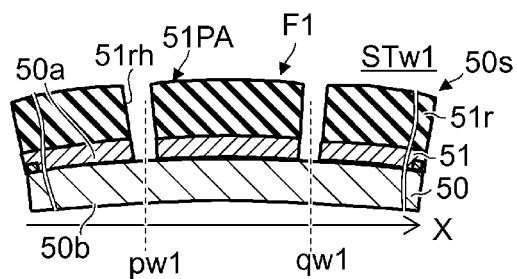
FIG. 11A and FIG. 11B are schematic sectional views exemplifying the operation of the processing system according to the third embodiment.
Figure 11B:
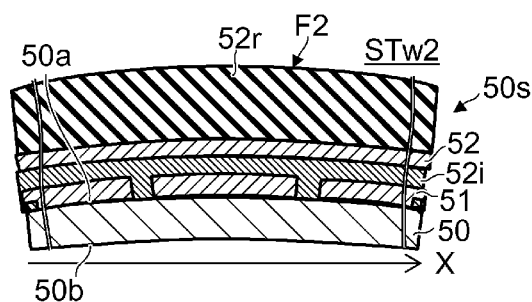

FIG. 11A and FIG. 11B are schematic sectional views exemplifying operation of the processing system according to the third embodiment. FIG. 11A illustrates Step MS1. In the first warpage state (first state STw1), the warpage of the substrate 50 (wafer 50s) is obtained. In this example, the first film F1 is the first resist film 51r.

FIG. 11B illustrates Step MS2. In the second warpage state (first state STw2), the warpage of the substrate 50 (wafer 50s) is obtained. In this example, the intermediate layer 52i, the second process layer 52, and the second resist film 52r are disposed on the first process layer 51. The second film F2 is the second resist film 52r. In Step MS2, the second film F2 is unpatterned, and may be patterned later.

Therefore, in the embodiment, the warpage detecting unit 20 detects the first warpage in the first state STw1 of the substrate 50, and the second warpage in the second state STw2 of the substrate 50. In the first state STw1, the first film F1 including the first pattern 51PA is disposed on the first surface 50a of the substrate 50. In the second state STw2, the second film F2 is disposed on the first surface 50a.

In this example, in the first state STw1, the first process layer 51 is disposed on the first surface 50a, and the first film F1 is disposed on the first process layer (refer to FIG. 11A). In the second state STw2, the second process layer 52 is disposed on at least a part of the first process layer 51, and the second film F2 is disposed on the second process layer 52 (refer to FIG. 11B).

Based on a value in accordance with a difference between the first warpage and the second warpage, the processing unit 70 processes the second film F2 (in this example, second resist film 52r), and the second pattern 52PA is formed. For example, an exposing condition of the exposing device 71 included in the processing unit 70 is adjusted on the basis of a value in accordance with a difference between the first warpage and the second warpage.

In the embodiment, the second pattern 52PA is formed on the basis of the difference of the warpage of the substrate 50. Accordingly, in the second pattern 52PA, the alignment error with the first pattern 51PA can be reduced. A processing system with small alignment error results, leading to small devices, high storage density of storage devices, and high manufacturing yield.

Figure 12A:
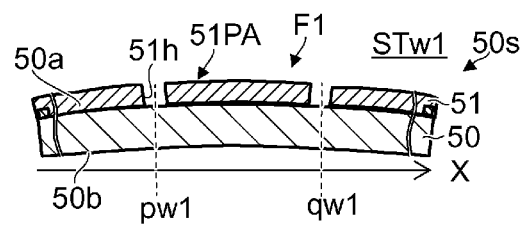
FIG. 12A and FIG. 12B are schematic sectional views exemplifying another operation of the processing system according to the third embodiment.
Figure 12B:
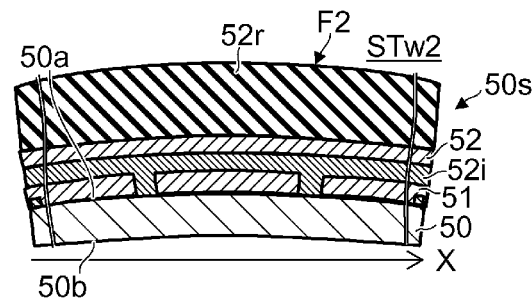

FIG. 12A and FIG. 12B are schematic sectional views exemplifying another operation of the processing system according to the third embodiment.

FIG. 12A illustrates Step MS1. In the first warpage state (first state STw1), the warpage of the substrate 50 (wafer 50s) is obtained. In this example, the first film F1 is the first process layer 51.

FIG. 12B illustrates Step MS2. In this example, the second film F2 is the second resist film 52r. In Step MS2, the second film F2 unpatterned, and may be patterned later.

In this example, the first film F1 is the first process layer 51 disposed on the first surface 50a in the first state STw1 (refer to FIG. 12A). In the second state STw2, the second process layer 52 is formed on at least a part of the first process target layer 51, and the second film F2 (second resist film 52r) is disposed on the second process layer 52 (refer to FIG. 12B).

Figure 13A:
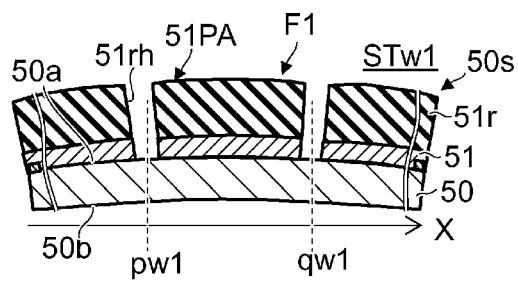
FIG. 13A and FIG. 13B are schematic sectional views exemplifying the other operation of the processing system according to the third embodiment.
Figure 13B:
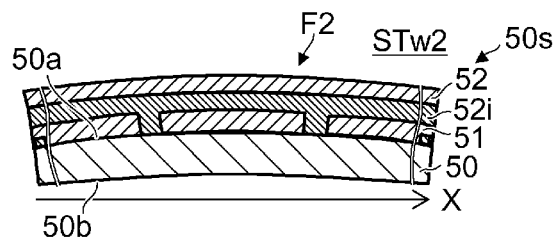

FIG. 13A and FIG. 13B are schematic sectional views exemplifying another operation of the processing system according to the third embodiment.

FIG. 13A illustrates Step MS1. In the first warpage state (first state STw1), the warpage of the substrate 50 (wafer 50s) is obtained. In this example, the first film F1 is the first resist film 51r.

FIG. 13B illustrates Step MS2. In this example, the second film F2 is the second process layer 52. In Step MS2, the second film F2 is unpatterned, and may be patterned later.

In this example, in the first state STw1, the first process layer 51 is disposed on the first surface 50a, and the first film F1 (first resist film 51r) is disposed on the first process layer 51 (refer to FIG. 13A). The second film F2 is the second process layer 52 formed on the first process layer 51, after the first film F1 (first resist film 51r) is removed (refer to FIG. 13B).

The processing unit 70 forms the second pattern 52PA by processing the second film F2 (in this example, second process layer 52), based on a value in accordance with a difference between the first warpage and the second warpage. At this time, based on a value in accordance with a difference between the first warpage and the second warpage, a processing condition of the second resist film 52r is adjusted. An exposing condition of the exposing device 71 included in the processing unit 70 is adjusted, based on a value in accordance with a difference between the first warpage and the second warpage. The second process layer 52 is processed on the basis of a pattern of the second resist film 52r, which is adjusted and formed.

Figure 14A:
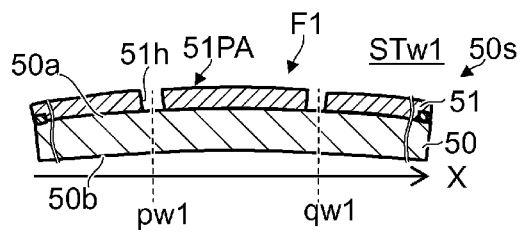
FIG. 14A and FIG. 14B are schematic sectional views exemplifying still another operation of the processing system according to the third embodiment.
Figure 14B:
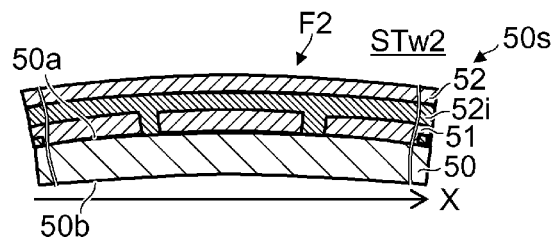

FIG. 14A and FIG. 14B are schematic sectional views exemplifying still another operation of the processing system according to the third embodiment.

FIG. 14A illustrates Step MS1. In the first warpage state (first state STw1), the warpage of the substrate 50 (wafer 50s) is obtained. In this example, the first film F1 is the first process layer 51.

FIG. 14B illustrates Step MS2. In this example, the second film F2 is the second process layer 52. In Step MS2, the second film F2 is unpatterned, and may be patterned later.

Therefore, in this example, the first film F1 is the first process layer 51 formed on the first surface 50a. At least a part of the second film F2 (second process layer 52) is disposed on at least a part of the first process layer 51.

First Alignment Error Example

FIG. 3 was described above. The process of FIG. 3 will now be used to describe an example of deriving an alignment error between patterns.

In Step MS1 of FIG. 3, warpage (first warpage state) of the wafer is obtained when the wafer is not forced to be flat. At least one of a front surface and a rear surface of the substrate 50 is evaluated to obtain the first warpage state. Also, while the wafer is not forced to be flat, a first chip arrangement (for example, position of pattern: position pf1, position qf1, or the like) formed in the first lithography (Step LI1), and a first pattern shape is obtained. At this time, a temperature distribution of the wafer may also be obtained. The first pattern shape is corrected based on the first warpage, detected pattern shape, and optionally temperature distribution, to obtain a pattern shape in a third warpage state. The third warpage state may be an "ideal adhesion" state where the substrate 50 is removably adhered to a stage, the third warpage state may be a flat state, or the third warpage state may be another reference state. The process of correcting the first pattern shape uses, as input, the detected first pattern shape, the detected first warpage state, and optionally the temperature distribution. The process produces, as output, the corrected first pattern shape in the reference warpage state. Deriving from the first input to the first output corresponds to a first warpage correction. The first output is stored in, for example, a storage device (for example, first database 41, second database 42, and the like).

Further, in Step MS2 of FIG. 3, the second warpage state of the wafer is obtained while the wafer is not forced to be flat. At least one of the front surface and a rear surface of the wafer is evaluated to obtain the second warpage state. Also, while the wafer is not forced to be flat, a second chip arrangement (for example, position of pattern: position pf1, position qf1, and the like) formed in the second lithography (Step LI2) and a second pattern shape are obtained. At this time, the temperature distribution of the wafer may be obtained. The second pattern shape is corrected based on the second warpage, detected second pattern shape, and optionally temperature distribution, to obtain a pattern shape in the third warpage state. The process of correcting the second pattern shape uses, as input, the detected second pattern shape, the detected second warpage state, and optionally the temperature distribution. The process produces, as output, the corrected second pattern shape in the reference, or third, warpage state. Deriving from the second input to the second output corresponds to a second warpage correction. The second output is stored in, for example, a storage device (for example, first database 41, second database 42, and the like).

A difference between the first output and the second output is obtained. From the difference, further, components of translation of the wafer and components of rotation of the wafer are removed. From the difference, components of magnification of the wafer may also be removed. The difference between the two corrected pattern shapes, with components of translation, rotation, magnification, and other external effects removed, yields alignment error of the two patterns. The alignment error includes, for example, a difference of relative positions between the first chip arrangement formed in the first lithography (Step LI1) and the second chip arrangement formed in the second lithography (Step LI2).

Second Example

Another example (second example) of deriving a difference (alignment error) of positions of patterns will be described.

In the second example, as the first input, in addition to the first warpage state, the first chip arrangement formed in the first lithography (Step LI1), and the first pattern shape, position information of a reference point (first reference point information) is used to obtain the first warpage correction.

Also, as the second input in the second example, in addition to the second warpage state, the second chip arrangement formed in the second lithography (Step LI2), and the second pattern shape, position information of a reference point (second reference point information) is further used to obtain the second warpage correction.

As in the first example, a difference between the first output and the second output is obtained to determine alignment error. The alignment error in this case also includes a difference of relative positions between the first chip arrangement formed in the first lithography (Step LI1) and the second chip arrangement formed in the second lithography (Step LI2).

In this example, when the first reference point information and the second reference point information are used, components of translation of the wafer, components of rotation of the wafer, and components of magnification of the wafer are removed.

Third Example

FIG. 9 was described above. The process of FIG. 9 will now be used to describe an example of monitoring and managing performance of the exposing device 71.

In Step MS1 of FIG. 9, the first warpage state of the wafer is obtained, while the wafer is not forced to be flat, by evaluating at least one a front surface of a rear surface of the wafer (substrate 50). Also while the wafer is not forced to be flat, the first chip arrangement (for example, position of pattern: position pf1, position qf1, and the like) formed in the first lithography (Step LI1), and the first pattern shape are obtained. At this time, the temperature distribution of the wafer may be obtained. The first warpage correction is determined and stored as in the above examples.

The magnitude of the correction in the first output is compared to a reference value or to a prior correction to determine whether the exposing device 71 is performing within tolerance. A large correction, or a large change in the magnitude of the correction, can indicate that the exposing device 71 has changed in a way that should be addressed. The exposing device 71 may be recalibrated if the correction is outside an acceptable tolerance.

In the third example, measurement of the warpage of the wafer and measurement of the first chip arrangement and the first pattern shape may be performed by different devices. The temperature distribution may be obtained using the same device used for measuring the first chip arrangement and the first pattern shape. For example, measurement of the first chip arrangement and the first pattern shape may be obtained by determining deviation from a design value of a position of the pattern measured by interferometer.

Fourth Example

An example of a feed-forward process relating to the process of FIG. 9 will now be described.

In Step MS1 of FIG. 9, the first warpage state of the wafer is obtained, while the wafer is not forced to be flat, by evaluating at least one a front surface of a rear surface of the wafer (substrate 50). Also while the wafer is not forced to be flat, the first chip arrangement (for example, position of pattern: position pf1, position qf1, and the like) formed in the first lithography (Step LI1) and the first pattern shape are obtained. At this time, the temperature distribution of the wafer may be obtained. The first input and output described in the above examples are created and stored.

Based on the first output, and for example, information (for example, design position of chip arrangement, pattern shape, and the like) stored in the storage device, a condition in a subsequent lithography (second lithography) can be adjusted. That is, the feed-forward is performed.

For example, the correction value can be used to adjust positional deviation of a subsequent wafer exposure in a second lithography. For example, a distortion component of the exposure can be corrected by shifting and exposing at least any one of an original plate and the wafer stage based on the correction value.

Fifth Example

In a fifth example hereinafter, a feed-forward process based on the process of FIG. 10 will be described.

As illustrated in FIG. 10, and as described in the above examples, the first and second input and output are created and stored.

Based on the second output, and for example, information (warpage of wafer, first chip arrangement, and first pattern shape) stored in the storage device, a condition in the second lithography (Step LI2), as described above, can be adjusted. That is, the feed-forward is performed.

The fifth example is effective, compared to the fourth example, when the pattern formed in the first lithography (Step LI1) is less likely to be recognized in Step MS2.

Sixth Example

In the sixth example, the described process relating to FIG. 10 is also used to monitor a film forming process.

For example, in Step MS1 of FIG. 10, the first and second input and output, as described in the above examples, is created and stored.

A difference between the first output and the second output, representing alignment error in the pattern, is obtained. The alignment error can be used to indicate a change or abnormality of either the etching or film-forming process.

In the embodiment, for example, the design position of the pattern may be expressed as a sum of a position in the wafer coordinate system and a position of a measurement field coordinate system. For example, the wafer coordinate system is used for expressing a position of the center of the measurement field coordinate system. The measurement field coordinate system is used for expressing a position of a measuring point. In the wafer coordinate system, the center of the wafer 50s is set to the original point. Let xw and yw indicate positions in the wafer coordinate system, where xw=0, yw=0 is the center of the wafer. In the measurement field coordinate system, the center of the measurement field is set to an original point. Let xf and yf indicates positions in the measurement field coordinate system, where xf=0, yf=0 is the center of the measurement field. Let $\xi$ and $\eta$ indicate a measuring equipment coordinate system, where $\xi=0$, $\eta=0$ is an origin point of the measuring equipment, typically a point on the stage. The measuring equipment coordinate system may be defined by a value read by an interferometer. For example, let values that are corrected based on data of the warpage of the wafer 50s so as to represent positions of measuring points when the wafer 50s is removably adhered to the stage and in a flat state be values in the ($\xi,\eta$) coordinate system. The data of the warpage of the wafer 50s is data measured by, for example, the inside of the measuring equipment or the other device different from the measuring equipment. When the wafer is removably adhered to the stage, there is typically no friction between the stage and a rear surface of the wafer 50s.

For example, M measurement fields are defined on the surface of the wafer 50s (where M is an integer equal to or greater than two). In one measurement field, N measuring points are provided (N is an integer equal to or greater than two). As described above, in the first lithography (Step LI1), a resist pattern of the first pattern 51PA is formed the first resist film 51r (first film F1) on the flat wafer 50s. In each of the M measuring fields, a position of N measuring points is measured.

The jth measuring point of the ith measurement field is referred to as measuring point (i,j). Each measuring field i has a position in the wafer coordinate system of $(xw_i, yw_i)$ (i=1, . . . , M), and each measuring point j has a position in its particular measurement field coordinate system of $(xf_j, yf_j)$ (j=1, . . . , N).

Consider measurement of the first warpage state in first state STw1 (at step MS1). Let a measured result of the measuring equipment of the position of the measuring points (i,j) be $(\xi_{ij}, \eta_{ij})$ (i=1, . . . , M, and j=1, . . . , N) in the measuring equipment coordinate system. To reduce an error of the measuring equipment, for a position of one measuring point, data which is measured in multiple by rotating the wafer 50s may be used. For example, measurement may be performed in multiple so that the wafer 50s is positioned at zero degrees, 90 degrees, 180 degrees, or 270 degrees of rotation.

When the wafer 50s is positioned on the stage of the measuring equipment, the wafer 50s might not be flat. In such a case, warping may be generated due to weight of the wafer 50s. This warping may be calculated by, for example, a finite element method. Otherwise, the warping may be measured using a test substrate. The measured values $(\xi_{ij}, \eta_{ij})$ of the warping can be used to correct for the warping.

For example, the measured values $(\xi_{ij}, \eta_{ij})$ of the warping transform as follows.

$$\xi_{ij} = T_\xi - R(yw_i + yf_j) + xw_i + xf_j + dxw_i + dxf_{ij} + \delta_{ij} (i=1, \ldots, M)$$

$$\eta_{ij} = T_\eta + R(xw_i + xf_j) + yw_i + yf_j + dyw_i + dyf_{ij} + \epsilon_{ij} (j=1, \ldots, N)$$

In the above description, "$T_\xi$" and "$T_\eta$" are a distance between the origin of the measuring equipment coordinate system and the center of the wafer 50s when the wafer 50s is loaded on the stage; "R" is an angle between the wafer coordinate system and the measuring equipment coordinate system; $dxw_i$ and $dyw_i$ are deviation of the position of the ith measurement field from a design value; $dxf_{ij}$ and $dyf_{ij}$ are deviation of the measurement point (i,j) from a design value thereof, with the deviations $(dxw_i, dyw_i)$ removed. $\delta_{ij}$ and $\epsilon_{ij}$ are errors of the measuring equipment.

For example, $\{dxw\}$, $\{dyw\}$, $\{dxf\}$, $\{dyf\}$, $T_\xi$, $T_\eta$, and R are calculated using Lagrange multiplier method.

For example, $\{dxw\}^{(1)}$, $\{dyw\}^{(1)}$, $\{dxf\}^{(1)}$, $\{dyf\}^{(1)}$, $T_\xi^{(1)}$, $T_\eta^{(1)}$, and $R^{(1)}$ indicate the positions of the first pattern 51PA by the first lithography (Step LI1). For example, $\{dxw\}^{(2)}$, $\{dyw\}^{(2)}$, $\{dxf\}^{(2)}$, $\{dyf\}^{(2)}$, $T_\xi^{(2)}$, $T_\eta^{(2)}$, and $R^{(2)}$ indicate the positions regarding the second pattern 52PA by the second lithography (Step LI2). Relative deviation between the positions corresponds to the alignment error.

In one example, a thickness of the wafer 50s is 775 μm. A size of the wafer 50s is, for example, 300 mm. Also, right after the first lithography (Step LI1), an amount of warpage is zero. That is, in the first warpage state (first state STw1), the warpage of the wafer 50s is zero (Step MS1). Also, after Step FM1 (forming film), alignment is performed by translation and rotation and the second lithography (Step LI2) is performed. Also, in the second lithography, the position of the second pattern 52PA is calculated. The warpage of the wafer 50s is calculated in Step MS2, and it is assumed that a curvature is $3.56 \times 10^{-9}$ (/μm).

At this time, in Step MS2, the first pattern 51PA of the first lithography may be adjusted according to a predetermined magnification, which may be computed using the Stoney method as $(-775 \mu m/6) \times (3.56 \times 10^{-9} /\mu m) \times 10^6 = -0.46$ ppm.

In this case, the alignment errors between the first lithography and the second lithography, without compensating for magnification, are indicated by $$\{dxw^{(2)}_i - (-0.46 \text{ ppm})xw_i - dxw^{(1)}_i\},$$

$$\{dxf^{(2)}_{i,j} - (-0.46 \text{ ppm})xf_{i,j} - dxf^{(1)}_{i,j}\},$$

$$\{dyw^{(2)}_i - (-0.46 \text{ ppm})yw_i - dyw^{(1)}_i\}, \text{ and}$$

$$\{dyf^{(2)}_{i,j} - (-0.46 \text{ ppm})yf_{i,j} - dyf^{(1)}_{i,j}\}.$$

The alignment error is obtained without measuring the first pattern 51PA, after the second lithography.

If alignment of magnification is performed in the second lithography (Step LI2), in addition to alignment of translation and rotation, the alignment errors are indicated by simple coordinate differences $$\{dxw^{(2)}_i - dxw^{(1)}_i\},$$

$$\{dxf^{(2)}_{i,j} - dxf^{(1)}_{i,j}\},$$

$$\{dyw^{(2)}_i - dyw^{(1)}_i\}, \text{ and}$$

$$\{dyf^{(2)}_{i,j} - dyf^{(1)}_{i,j}\}.$$

Moreover, in the specification, "vertical" and "parallel" not only include strict vertical and strict parallel, but also include variation in, for example, a manufacturing process, and may be substantial vertical and substantial parallel.

Hitherto, the exemplary embodiments are described with reference to specific examples. However, the exemplary embodiments are not limited to the specific examples. For example, a specific configuration of each element such as the warpage detecting unit, the pattern detecting unit, the supporting unit, the stage, and the processing unit included the pattern accuracy detecting apparatus is included a range of the exemplary embodiment as long as the same effects can be obtained in a same way that the skilled in the art performs the exemplary embodiment by appropriately selecting from a known range.

In addition, combination of two or more components of each specific example within a technically available range is also included in the range of the exemplary embodiment as long as it includes a scope of the exemplary embodiment.

In addition, based on the pattern accuracy detecting apparatus and the processing system described as the exemplary embodiments, all of the pattern accuracy detecting apparatuses and the processing systems which are appropriately changed in design by the skill in the art are also included in the range of the exemplary embodiment as long as the it includes the scope of the exemplary embodiment.

In addition, in a spirit of the exemplary embodiment, the skilled in the art conceives various modification examples and revising examples, and it is understood that these modification examples and revising examples are also belong to the range of the exemplary embodiment.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A pattern accuracy detecting apparatus comprising:
a stage for supporting a substrate;
an optical warpage detecting unit configured to measure a warpage of a substrate disposed on the stage;
an optical pattern detection unit configured to detect a position of a pattern on the substrate; and
a processing unit programmed to:
determine an alignment difference between a first position of a first pattern of a first film that is formed on the substrate by a first process and a second position of a second pattern of a second film that is formed on the substrate by a second process, wherein the first and second positions have been detected by the optical pattern detection unit,
determine a difference between a first warpage of the substrate that has been measured by the optical warpage detecting unit during the first process and a second warpage of the substrate that has been measured by the optical warpage detecting unit during the second process, and
correct the alignment difference based on the difference between the first warpage and the second warpage.

2. The apparatus according to claim 1, wherein the optical warpage detecting unit comprises a first shape detecting unit configured to measure a warpage of a first surface of the substrate disposed on the stage and a second shape detecting unit configured to measure a warpage of a second surface of the substrate disposed on the stage.

3. The apparatus according to claim 2, wherein each of the first and second shape detecting units is an optical reflection device.

4. The apparatus according to claim 1, further comprising:
a temperature detection unit.

5. The apparatus according to claim 4, wherein the temperature detection unit is a temperature distribution detector.

6. The apparatus according to claim 1, wherein the stage is configured to adhere a substrate thereto.

7. The apparatus according to claim 6, wherein the first warpage and the second warpage are measured by the optical warpage detecting unit when the substrate rests on one or more supporting units of the stage and is not adhered to the stage during the first and second processes, respectively.

8. The apparatus according to claim 7, wherein the first and second positions are detected by the optical pattern detection unit when the substrate is adhered to the stage during the first and second processes, respectively.

9. A substrate processing system comprising:
a warpage detecting unit configured to measure a warpage of a substrate;
a processor configured to determine a difference between a first warpage of the substrate in a first state and a second warpage of the substrate in a second state after the first state, which warpages have been measured by the warpage detecting unit, wherein a first film including a first pattern is disposed on a first surface of the substrate in the first state, and a second film is disposed on the first surface in the second state; and
a processing device configured to control a process for forming a second pattern by processing the second film based on the difference between the measured first warpage and the measured second warpage,
wherein the warpage detecting unit comprises a first shape detecting unit for detecting the warpage of a first side of the substrate and a second shape detecting unit for detecting the warpage of a second side of the substrate opposite from the first side.

10. The system according to claim 9, wherein the first shape detecting unit and the second shape detecting unit are each optical reflection devices.

11. The system according to claim 9, wherein the processing device includes at least one of an etch device and a lithography device.

12. The system according to claim 9, further comprising:
a temperature detecting unit.

13. The system according to claim 12, wherein the temperature detecting unit is a temperature distribution detector.

* * * * *